(12) United States Patent
Waggoner et al.

(10) Patent No.: US 7,408,062 B2
(45) Date of Patent: Aug. 5, 2008

(54) RIGIDIZED TRIMETHINE CYANINE DYES

(75) Inventors: Alan S. Waggoner, Pittsburgh, PA (US); Ratnakar B. Mujumdar, Pittsburgh, PA (US)

(73) Assignee: Carnegie Mellon University, Pittsburgh, PA (US)

(*) Notice: Subject to any disclaimer, the term of this patent is extended or adjusted under 35 U.S.C. 154(b) by 0 days.

(21) Appl. No.: 10/351,369

(22) Filed: Jan. 27, 2003

(65) Prior Publication Data

US 2003/0224391 A1 Dec. 4, 2003
US 2007/0243527 A9 Oct. 18, 2007

Related U.S. Application Data

(63) Continuation of application No. 09/639,941, filed on Aug. 17, 2000, now abandoned, which is a continuation of application No. 09/212,564, filed on Dec. 16, 1998, now Pat. No. 6,133,445, which is a continuation-in-part of application No. 08/992,212, filed on Dec. 17, 1997, now abandoned.

(51) Int. Cl.
C07D 491/22 (2006.01)
C07D 471/22 (2006.01)

(52) U.S. Cl. ............................ 546/36; 546/28; 546/33

(58) Field of Classification Search ................ 546/36, 546/28, 33
See application file for complete search history.

(56) References Cited

U.S. PATENT DOCUMENTS

| | | | |
|---|---|---|---|
| 3,679,427 A | 7/1972 | Lincoln et al. |
| 3,753,721 A | 8/1973 | Millikan et al. |
| 3,821,233 A | 6/1974 | Lincoln et al. |
| 3,854,956 A | 12/1974 | Lincoln et al. |
| 3,864,644 A | 2/1975 | Lincoln et al. |
| 3,904,637 A | 9/1975 | Lincoln et al. |
| 3,915,715 A | 10/1975 | Millikan et al. |
| 4,435,492 A | 3/1984 | Suzuki et al. |
| 4,524,128 A | 6/1985 | Edwards et al. |
| 4,600,625 A | 7/1986 | Abe et al. |
| 4,847,385 A | 7/1989 | Kusakata et al. |
| 4,981,977 A | 1/1991 | Southwick et al. |
| 5,008,401 A | 4/1991 | Utsunomiya et al. |
| 5,268,486 A | 12/1993 | Waggoner et al. |
| 5,486,616 A | 1/1996 | Waggoner et al. |
| 5,569,766 A | 10/1996 | Waggoner et al. |
| 5,747,233 A | 5/1998 | Lonsky et al. |
| 6,048,982 A | 4/2000 | Waggoner |
| 6,083,485 A | 7/2000 | Licha et al. |
| 6,133,445 A | 10/2000 | Waggoner et al. |
| 6,180,085 B1 | 1/2001 | Achilefu et al. |
| 6,180,086 B1 | 1/2001 | Achilefu et al. |
| 6,180,087 B1 | 1/2001 | Achilefu et al. |
| 6,183,726 B1 | 2/2001 | Achilefu et al. |
| 6,190,641 B1 | 2/2001 | Achilefu et al. |
| 6,686,145 B1 * | 2/2004 | Waggoner et al. ............. 435/5 |

FOREIGN PATENT DOCUMENTS

| | | |
|---|---|---|
| DE | 2213715 | 10/1972 |
| DE | 43 41 618 | 6/1995 |
| EP | 0 747 448 A2 | 12/1996 |
| EP | 0 747 448 A3 | 12/1996 |
| EP | 0 747 700 | 12/1996 |
| GB | 412309 | 6/1934 |
| GB | 811876 | 4/1959 |
| WO | WO97/17471 | 5/1997 |
| WO | WO99/31181 | 6/1999 |
| WO | WO 02/26891 | 4/2002 |

OTHER PUBLICATIONS

O'Brien et al., Carbocyanine Dyes and the Energy-Transfer Mechanism of Spectral Sensitization, vol. 18, No. 1, Jan./Feb. 1974 pp. 76-85.

Mujumdar et al., 1993, Bioconjugate Chemistry, American Chemical Society Mar./Apr. 1993 vol. 4, No. 2 pp. 105-111 Cyanine Dye Labeling Reagents: Sulfoindocyanine Succinimidyl Esters.

Tian et al., J. of Photographic Science, 40 (1992) No. 4, pp. 100-104 Fluorescence Quenching of Cyanine Dyes Adsorbed onto the Surface of Colloid Semiconductors.

Tian H., Fluorescence Lifetimes of Supersensitizing Systems and Dyes Adsorbed Onto TiO2, J. Photochem. Photobiol. A 65(2)399-407, 1992.

Rosenstock, "2,3-Dimethyl-3H-indole-3-acetic Acid", Notes, Research Laboratories, The National Drug Company, (Dec. 1966), vol. 3, pp. 537.

Eggers et al., "A Spiroindolinopyran with Switchable Optical Activity", Chem. Int. Ed. Eng., (1997) 36, No. 8, pp. 881-883.

Eggers et al., "Synthesis of the First Chiral Bisindolyl Monomethinium Cyanine Dyes", Liegis Ann., 1996, 979-983.

Reichardt, et al., "Herstellung, Struktur and Eigenschaften neuartiger kettensubstituierter und chiraler Trimethincyanin-Farbstoffe mit Indolin-Endgruppen", Chem. Ber. 123, 1990, 565-581.

Reichardt et al., "Syntheses, Absolute Configuration, Spectroscopic, and Chiroptical Properties of Chiral Dinuclear Tri- and Pentamethinium as well as Trinuclear [2.2.2]Heptamethinediium Cyanine Dyes with 3-sec-Butyl-1,3-dimethylindolyl End Groups", Liebigs Ann. 1995, 329-340.

(Continued)

Primary Examiner—Charanjit S. Aulakh
(74) Attorney, Agent, or Firm—Nixon & Vanderhye P.C.

(57) ABSTRACT

Disclosed are analogues of trimethine cyanine dyes, which are useful for importing fluorescent properties to target materials by covalent and non-covalent association.

4 Claims, 10 Drawing Sheets

OTHER PUBLICATIONS

Southwick, et al., "Cyanine Dye Labeling Reagents-Carboxymethylindocyanine Succinimidyl Esters", Cytometry 11:418-430 (1990).

Mujumdar, et al., "Cyanine Dye Labeling Reagents Containing Isothicyanate Groups", Ctytometry, 1989, No. 1, pp. 11-19.

* cited by examiner

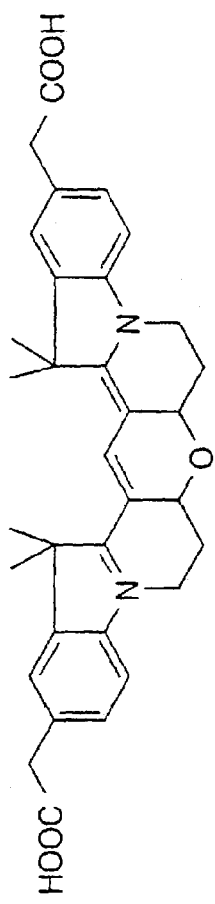
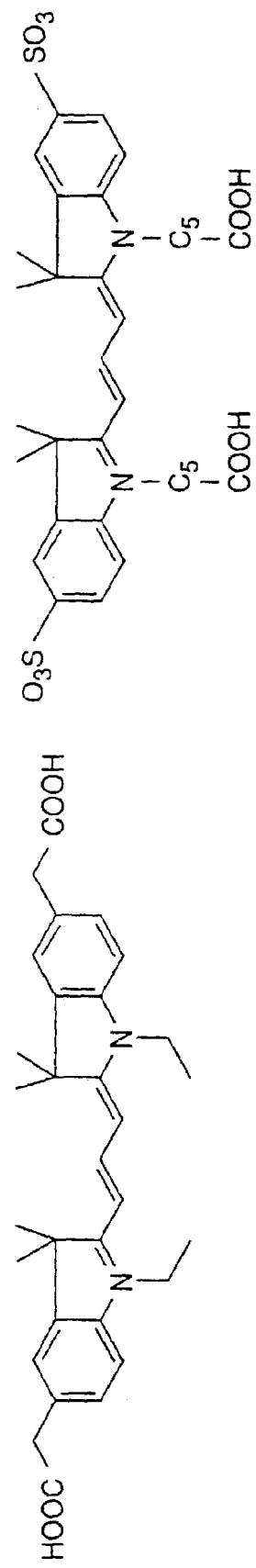
Fig. 2: Structures of Cyanine 3

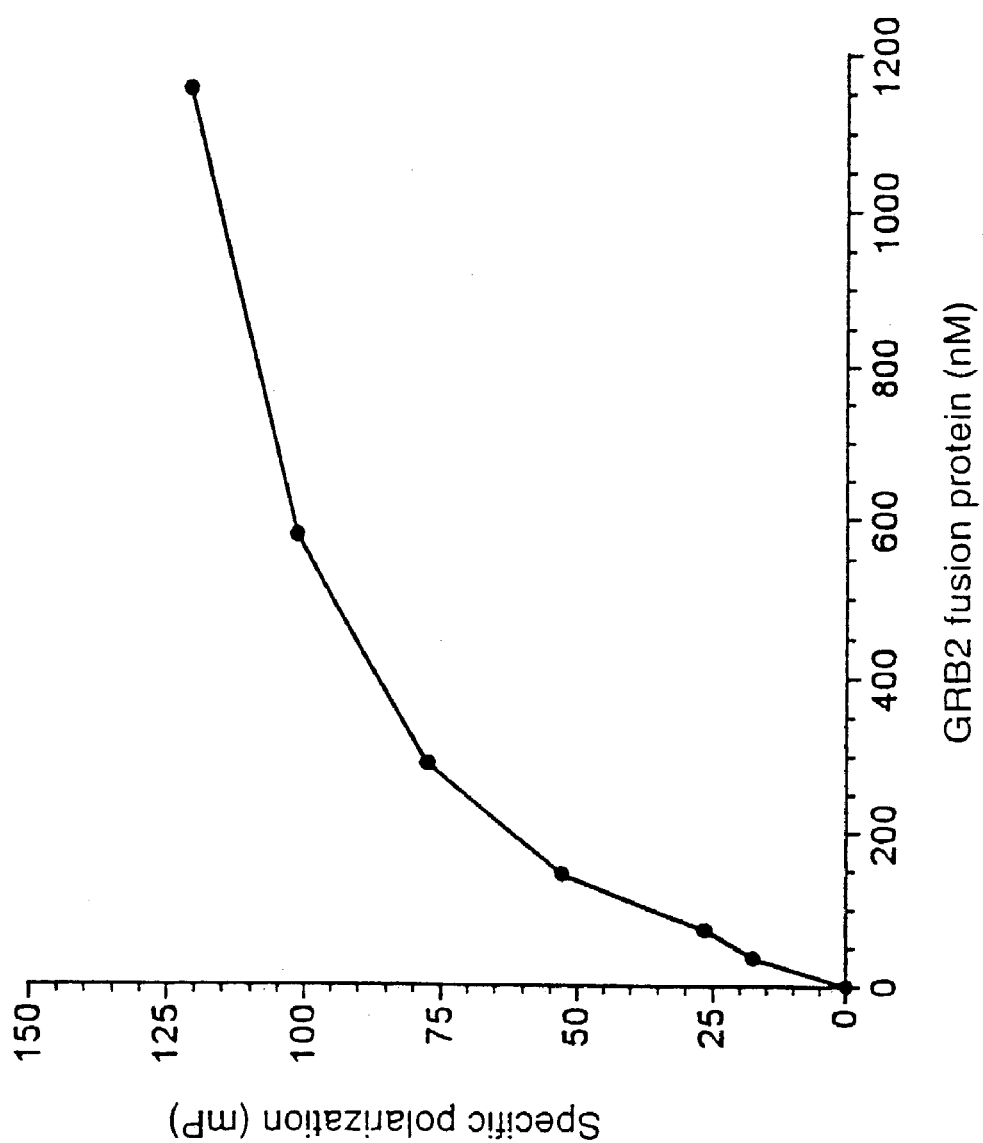
Fig. 6: Protein:Peptide Polarization Binding Assay (Example 12)

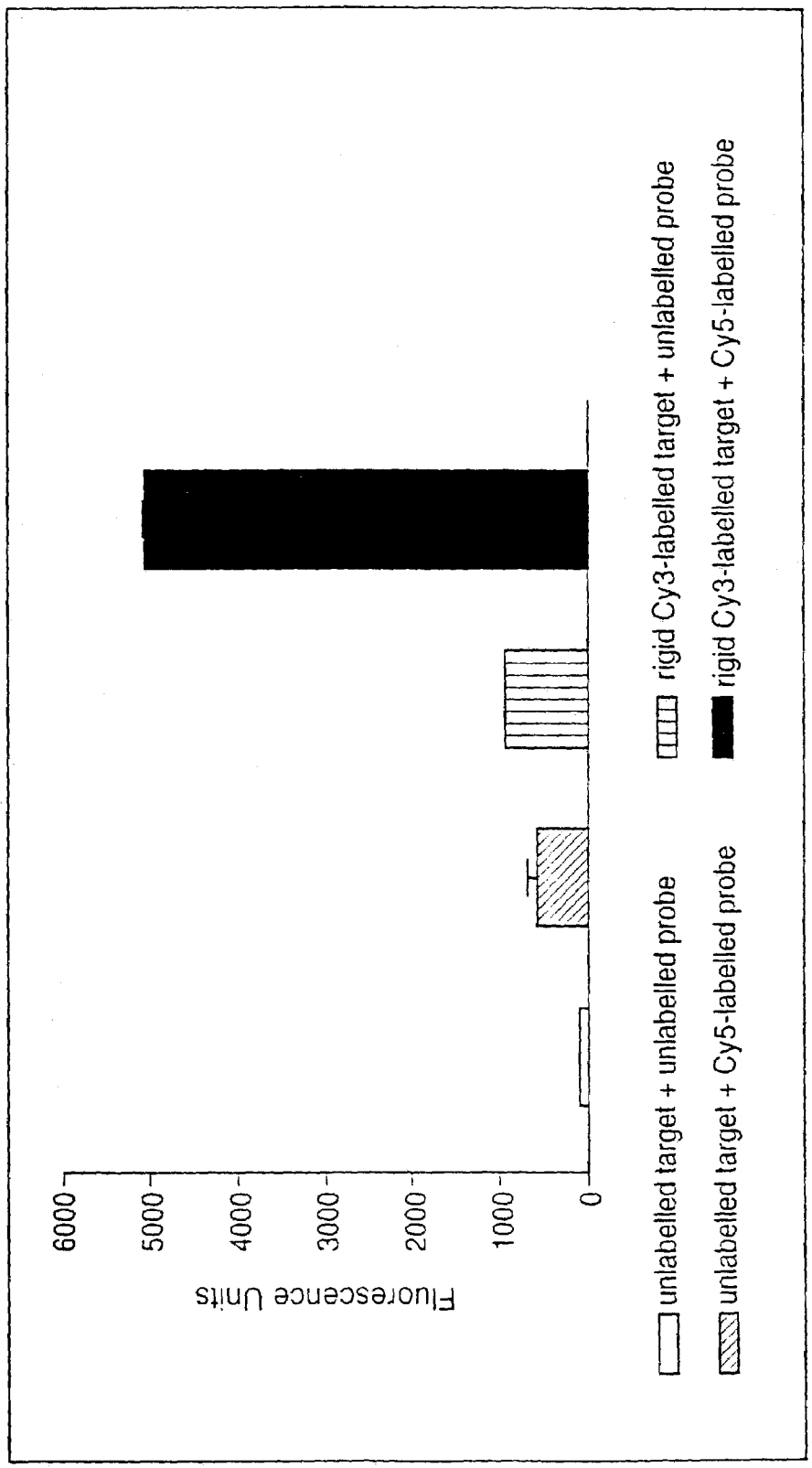

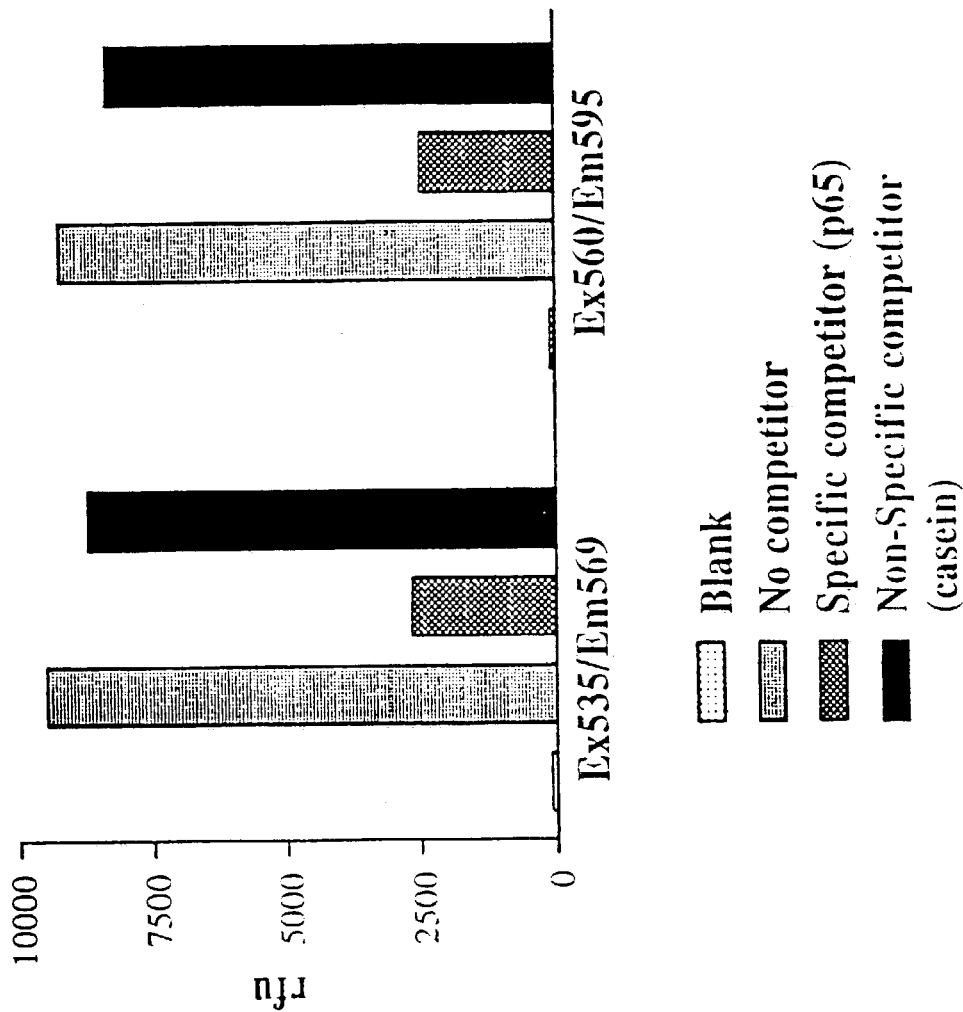

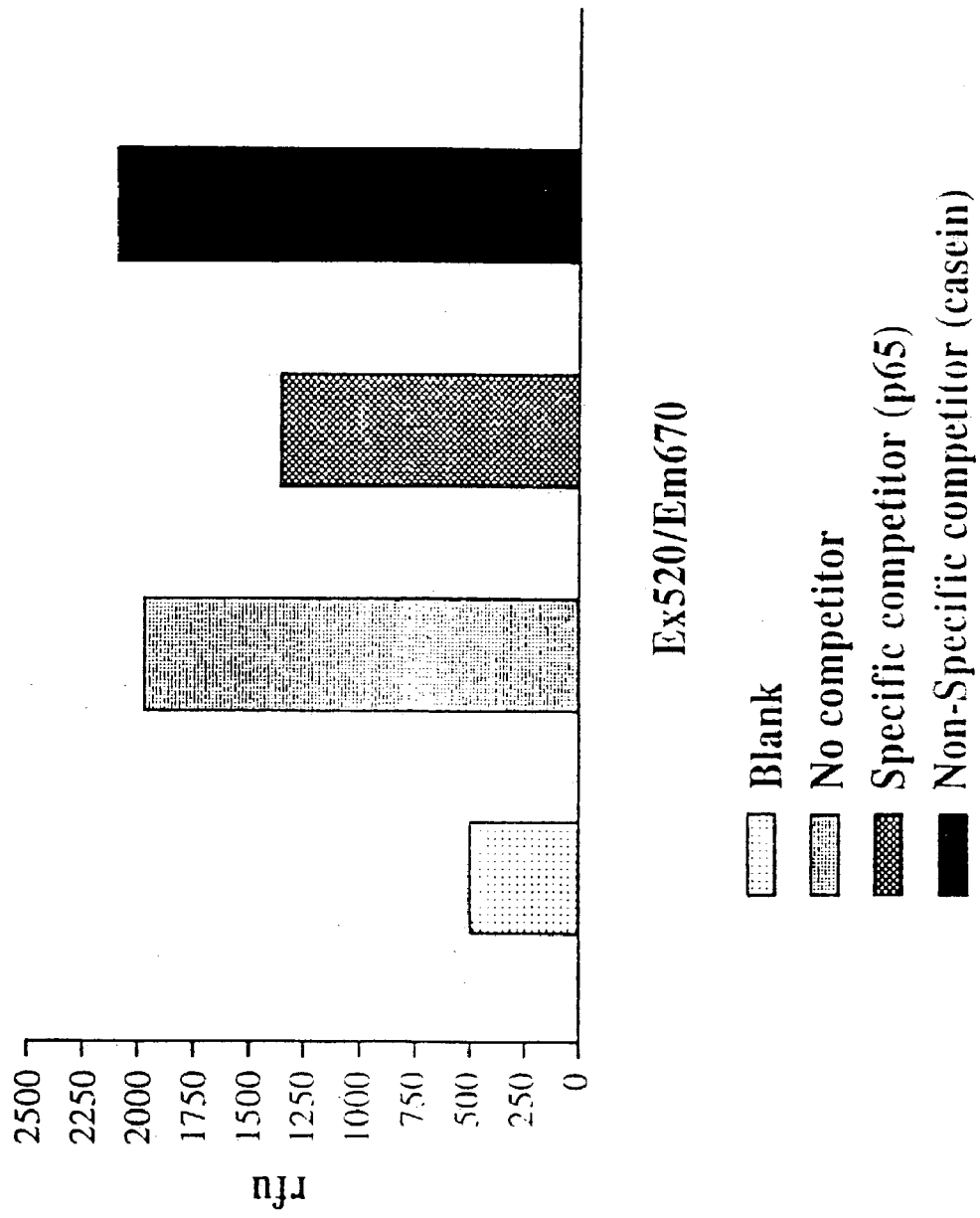
Fig. 9: Protein:DNA FRET Binding Assay (Example 15)

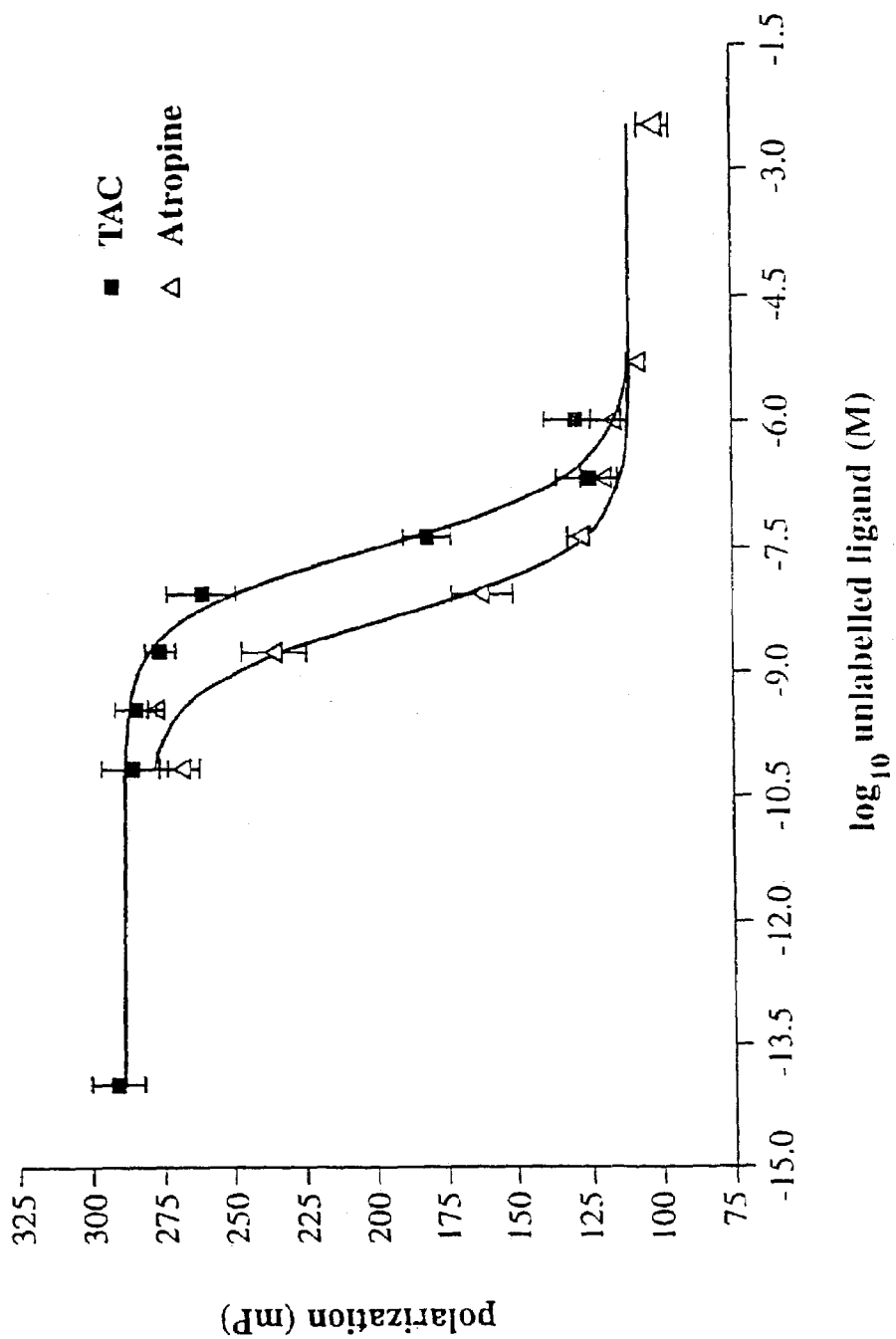
Fig. 10: Receptor Ligand Binding Assay using Fluorescence Polarization (Example 16)

SEQUENCE LISTING

```
<160> NUMBER OF SEQ ID NOS: 10

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: target
      oligonucleotide

<400> SEQUENCE: 1
tacccagacg agcaa                                                      15

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence:
      complementary unlabelled probe oligonucleotide

<400> SEQUENCE: 2
ttgctcgtct gggta                                                      15

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: second
      target oligonucleotide

<400> SEQUENCE: 3
tacccagacg agcaa                                                      15

<210> SEQ ID NO 4
<211> LENGTH: 15
<212> TYPE: DNA
<213> ORGANISM: Artificial Sequence
<220> FEATURE:
```

```
<223> OTHER INFORMATION: Description of Artificial Sequence: second
      probe oligonucleotide

<400> SEQUENCE: 4
ttgctcgtct gggta                                                        15

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence:
      biotinylated coding strand

<400> SEQUENCE: 5
gatctaggga cttccgcg                                                     19

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: unmodified
      coding strand

<400> SEQUENCE: 6
atccctgaaa ggcgccta                                                     18

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: coding
      strand modified with 5 prime terminal primary amine

<400> SEQUENCE: 7
gatctaggga ctttccgcg                                                    19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: unmodified
      non-coding strand

<400> SEQUENCE: 8
atccctgaaa ggcgcctag                                                    19

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Cy-5
      labelled coding strand

<400> SEQUENCE: 9
gatctaggga ctttccgcg                                                    19
```

```
<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: unmodified
      non-coding strand

<400> SEQUENCE: 10
atccctgaaa ggcgcctag                                                    19
```

RIGIDIZED TRIMETHINE CYANINE DYES

The present application is a continuation of U.S. Ser. No. 09/639,941, filed Aug. 17, 2000 (abandoned), which is a continuation of U.S. Ser. No. 09/212,564, filed Dec. 16, 1998 (now U.S. Pat. No. 6,133,445); and the present application is a continuation of PCT/US98/26665, filed 16 Dec. 1998, which designated the U.S. and is a continuation-in-part of U.S. Ser. No. 08/992,212, filed Dec. 17, 1997 (abandoned).

The present invention relates to rigidized trimethine cyanine dyes, their preparation, their use as fluorescent markers and in fluorescence energy transfer complexes and to materials labelled with them.

Fluorescent dyes are generally known and used for fluorescence labelling and detection of various biological and non-biological materials by procedures such as fluorescence microscopy, fluorescence immunoassay and flow cytometry. A typical method for labelling such materials with fluorescent dyes is to create a fluorescent complex by means of bonding between suitable groups on the dye molecule and compatible groups on the material to be labelled. In this way, materials such as cells, tissues, amino acids, proteins, antibodies, drugs, hormones, nucleotides, nucleic acids, lipids and polysaccharides and the like may be chemically labelled and detected or quantitated, or may be used as fluorescent probes which can bind specifically to target materials and detected by fluorescence detection methods.

Four commonly used classes of fluorescent dyes are those based on the fluorescein (green fluorescence), rhodamine (orange fluorescence), coumarin and pyrene (blue fluorescence) chromophores. Dyes based on fluorescein and rhodamine have a number of disadvantages. Fluorescein derivatives have a pH-sensitive absorption spectrum and fluorescence yield decreases markedly below pH 8. Rhodamine derivatives are hydrophobic and are difficult to use in aqueous media. They often show strong fluorescence quenching when bound to proteins.

U.S. Pat. No. 5,268,486 discloses luminescent mono- and polymethine cyanine dyes and related polymethine dyes such as merocyanine and styryl dyes which contain groups enabling them to covalently attached to amine, hydroxyl, aldehyde and sulphydryl groups on a target material. The compounds are disclosed as fluorescing in the green, orange, red and near infra-red regions of the spectrum.

U.S. Pat. No. 3,679,427 describes rigidized cyanine dyes which contain a trimethine chain as part of a rigid structure, as shown in formula (1):

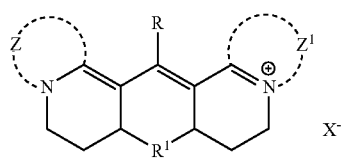

where each of Z and $Z^1$ represents the non-metallic atoms necessary to complete a heterocyclic nucleus of the type used in cyanine dyes; R represents a member selected from a hydrogen atom, an alkyl radical, or an aryl radical; $R^1$ represents a member selected from oxygen, sulphur, selenium or nitrogen. The subject dyes are reported to exhibit strong fluorescence and are useful spectral sensitizing dyes for photographic silver halide as well as being useful as colorant materials for a wide variety of compositions such as paints, lacquers, etc. However they are not described as fluorescent labelling dyes.

European Patent Application No. 747448 describes bis-heterocyclic monomethine cyanine dyes, rigidized by means of a bridging group between the nitrogen atoms of the heterocycles. Such compounds may be substituted with additional groups chosen to provide desirable solubility, reactivity and spectroscopic properties to the fluorescent compounds. The dyes can be used to covalently label a target material so as to impart fluorescent properties to that target. The monomethine rigidized cyanines are highly fluorescent and strongly light-absorbing dyes which emit in the near UV and blue (300–500 nm) region of the spectrum. None of the foregoing literature discloses fluorescent rigidized dye compounds that are capable of producing strong fluorescence in the green to orange region of the spectrum and also contain functional groups and/or solubilizing groups which render the dye suitable for covalent labelling, in particular to biological molecules and other target materials.

BRIEF DESCRIPTION OF THE DRAWINGS

FIG. 2 compares the rigidized dye structure of the dye of Example 1 with the structures of two open chain dyes.

FIG. 6 is a graph showing the result of a peptide polarization binding assay according to Example 12.2;

FIG. 7 is a graph showing the results of the nucleic acid FRET hybridization assay of Example 13.3;

FIG. 8 is a bar graph showing the results of a protein: DNA direct intensity binding assay according to the procedures of Example 14.2;

FIG. 9 is a bar graph showing the results of a protein: DNA FRET binding assay of Example 15.2; and FIG. 10 is a graph plotting specific polarization readings against concentration of unlabeled ligand following Example 16.2.

Figure 1:
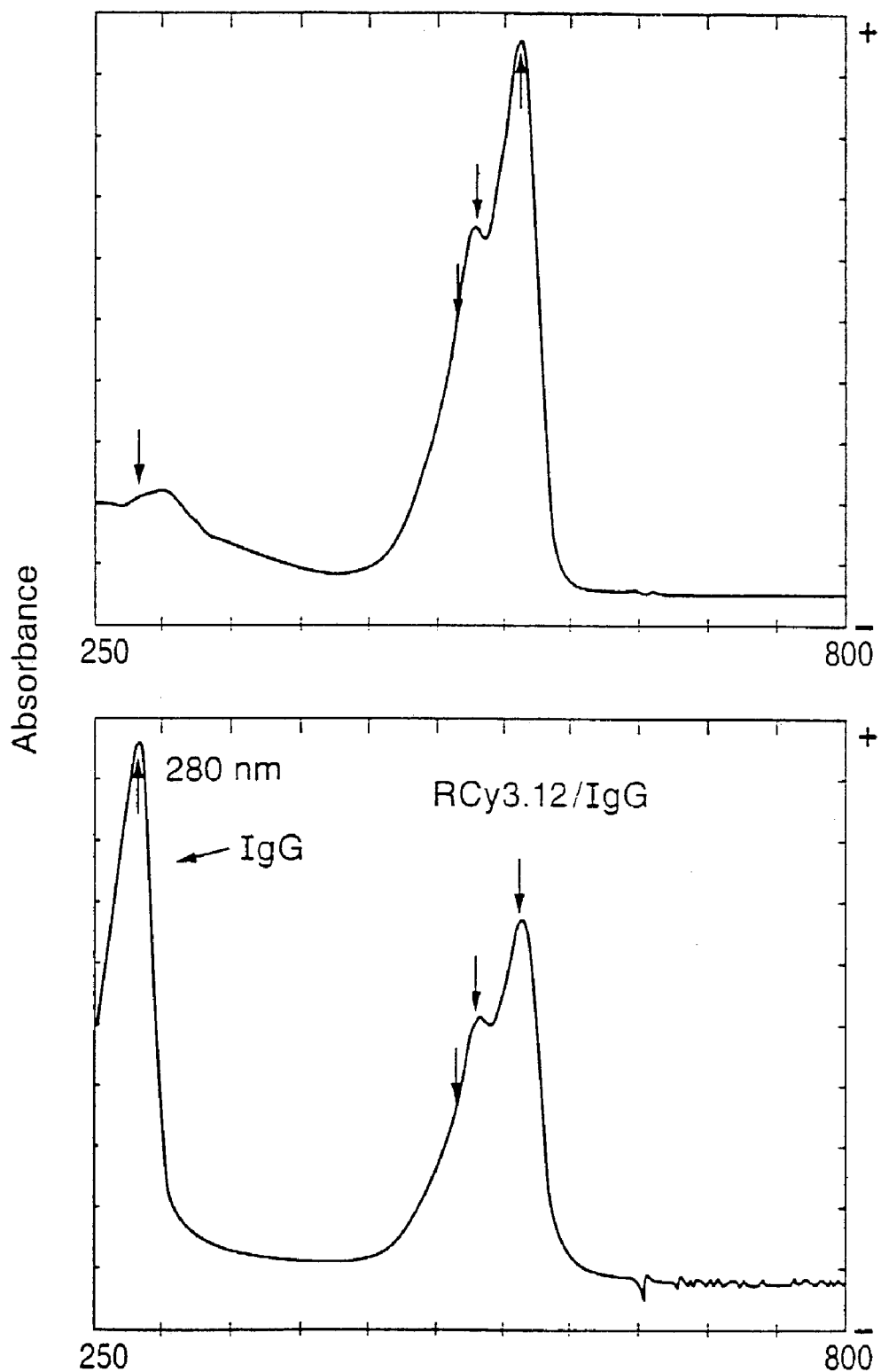
FIG. 1 is a graph showing the absorption spectra for a solution of the dye of Example 1 as compared to protein labeled with the dye in Example 1.6.

The present invention provides bright, highly fluorescent dye compounds which absorb and emit in the 450–600 nm region of the spectrum. They have rigid structures which are based on the trimethine cyanine chromophore and confer high quantum yields of fluorescence. Moreover, they can contain functional or reactive groups which may be used to covalently react with suitable groups on target materials such as biological molecules, and other materials. They are pH insensitive and thus they extend the range of useful fluorescent labelling reagents which can be used in fluorescent detection applications.

Accordingly, the present invention provides compounds of formula (2):

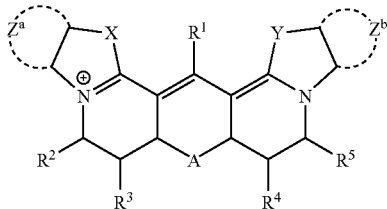

(2)

optionally substituted by groups $R^2$–$R^9$, wherein groups $R^6$, $R^7$, $R^8$ and $R^9$ are attached to the rings containing X and Y or, optionally are attached to atoms of the $Z^a$ and $Z^b$ ring structures;

$R^2$ to $R^9$ which are the same or different include —$R^1$ and -L-$R^{10}$ where $R^{10}$ is selected from neutral groups that reduce water solubility, polar groups that increase water solubility, functional groups that can be used in labelling reactions, reactive groups, electron donating and withdrawing groups that shift the absorption and emission wavelengths of the fluorescent molecule, lipid and hydrocarbon solubilising groups, and L is selected from the group consisting of a straight or branched $C_{1-20}$ alkyl chain, a $C_{2-20}$ monoether or polyether and a $C_{2-20}$ atom chain containing up to four secondary amide linkages;

$R^1$ is selected from hydrogen, aryl, heteroaryl, cyano, nitro, aldehyde, halogen, hydroxy, amino, quaternary amino, acetal, ketal, phosphoryl, sulphydryl, water-solubilizing groups, and alkyl groups optionally substituted by amino, $C_1$–$C_4$ alkyl-substituted amino, quaternary amino, carbonyl including aldehyde and ketone, acetal; ketal, halo, cyano, aryl, heteroaryl, hydroxyl, sulphonate, sulphate, carboxylate, amide, nitro, and groups reactive with amino, hydroxyl, aldehyde, phosphoryl, or sulphydryl groups;

A is selected from O, S and $NR^{11}$ where $R^{11}$ is the substituted amino radical:

where R' is selected from hydrogen, a $C_{1-4}$ alkyl and aryl and R" is selected from $C_{1-18}$ alkyl, aryl, heteroaryl, an acyl radical having from 2–7 carbon atoms, and a thiocarbamoyl radical.

X and Y may be the same or different and are selected from bis-$C_1$–$C_4$ alkyl and $C_4$–$C_5$ spiro alkyl substituted carbon, oxygen, sulphur, selenium, CH=CH, and N—W wherein N is nitrogen and W is selected from hydrogen, a group —(CH$^2$)$_n$$R^{12}$ where n is an integer from 1 to 26 and $R^{12}$ is selected from hydrogen, amino, aldehyde, acetal, ketal, halo, cyano, aryl, heteroaryl, hydroxyl, sulphonate, sulphate, carboxylate, substituted amino, quaternary amino, nitro, primary amide, substituted amide, and groups reactive with amino, hydroxyl, carbonyl, phosphoryl, and sulphydryl groups;

$Z^a$ and $Z^b$ each represent a bond or the atoms necessary to complete one, two fused or three fused aromatic rings each ring having five or six atoms, selected from carbon atoms and, optionally, no more than two oxygen, nitrogen and sulphur atoms;

provided that when X and Y are other than carbon, at least one of $R^1$–$R^9$ comprises a reactive group for covalent reaction with a functional group on a target material or comprises a functional group for covalent reaction with a reactive group on a target material, or, when X and Y are different and are selected from O and Se, at least one of $R^1$–$R^9$ is other than hydrogen, methyl, phenyl or naphthyl.

Preferred $R^{10}$ groups are selected from: hydrogen, halogen, amide, $C_1$–$C_6$ alkoxy, nitro, cyano, aryl, heteroaryl, sulphonate, quaternary ammonium, guanidinium, hydroxyl, phosphate, phosphonate, optionally substituted amino, azido, sulphydryl, carboxyl, carbonyl, reactive groups, for example, succinimidyl ester, isothiocyanate, anhydride, haloacetamide, maleimide, sulphonyl halide, phosphoramidite, acid halide, alkylimidate, hydrazide and carbodiimide; and groups reactive with amino, hydroxyl, aldehyde, phosphoryl, or sulphydryl groups.

Preferably $R^1$ is selected from hydrogen, aryl, heteroaryl, cyano, halogen, alkyl groups of twenty-six carbon atoms or less and —(CH$_2$)$_n$Q where 1<n<26 and Q is selected from amino, aldehyde, sulphydryl, hydroxyl and groups reactive with amino, hydroxyl, aldehyde, phosphoryl, or sulphydryl groups and $R^2$, $R^3$, $R^4$ and $R^5$ are hydrogen.

Suitably $R^{12}$ is selected from hydrogen, amino, sulphonate, carboxylate, aryl, hydroxyl, and groups reactive with amino, hydroxyl, carbonyl, phosphoryl, or sulphydryl groups.

Bis-substituted carbon includes bis $C_1$–$C_4$ alkyl groups and $C_4$–$C_5$ spiro alkyl groups.

Alkyl is a straight or branched chain alkyl group containing from 1–26 carbon atoms, suitably containing from 1–12 carbon atoms, preferably from 1–6 carbon atoms.

Aryl is an aromatic substituent containing one or two fused aromatic rings containing 6–10 carbon atoms, for example phenyl or naphthyl. The aryl may be optionally and independently substituted by one or more groups selected from groups —$R^{10}$ and -L-$R^{10}$ as hereinbefore defined.

Heteroaryl is a mono- or bicyclic 5–10 membered aromatic ring system containing at least one and no more than 3 heteroatoms which may be selected from N,O and S. The heteroaryl may be optionally and independently substituted by one or more groups selected from groups —$R^{10}$ and -L-$R^{10}$ as hereinbefore defined.

Aralkyl is a $C_1$–$C_5$ alkyl group substituted by an aryl or heteroaryl group.

Halogen and halo-groups are those selected from fluorine, chlorine, bromine and iodine.

Specific examples of the groups $R^1$–$R^9$ and $R^{11}$ and the groups with which those R-groups will react are provided in Table 1. In the alternative, the $R^1$–$R^9$ and $R^{11}$ may be the functional groups of Table 1 which would react with the reactive groups of a target molecule.

TABLE 1

Possible Reactive Substituents and Sites Reactive Therewith

| Reactive Groups | Corresponding Functional Groups |
|---|---|
| succinimidyl esters | primary amino, secondary amino, hydroxyl |
| anhydrides | primary amino, secondary amino, hydroxyl |
| acyl azides | primary amino, secondary amino |
| isothiocyanates, isocyanates | amino, thiol, hydroxyl |

TABLE 1-continued

Possible Reactive Substituents and Sites Reactive Therewith

| Reactive Groups | Corresponding Functional Groups |
| --- | --- |
| sulphonyl chlorides, sulphonyl fluorides | amino, hydroxyl |
| substituted hydrazines, substituted hydroxylamines | aldehydes, ketones |
| acid halides | amino, hydroxyl |
| haloacetamides, maleimides | thiol, imidazoles, hydroxyl, amino |
| carbodiimides | carboxyl groups |
| phosphoramidite | hydroxyl |

In addition to those groups listed in Table 1, a number of other groups are possible as reactive substituent in the $R^1$–$R^9$ and $R^{11}$ positions of the compounds of the present invention. For example, the reactive groups which are especially useful for labelling target components with available amino and hydroxy functional groups include:

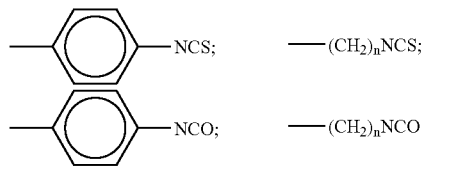

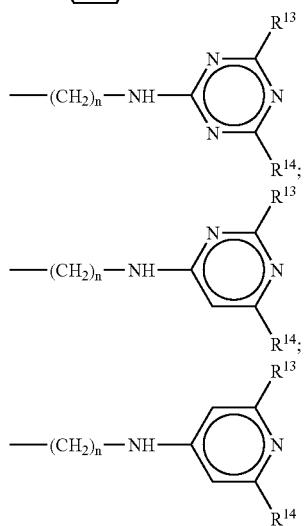

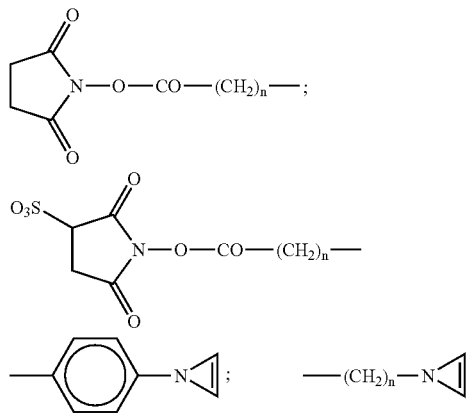

where n=0 or an integer from 1–10 and at least one of $R^{13}$ or $R^{14}$ is a leaving group such as I, Br, or Cl.

Specific examples of possible $R^1$–$R^9$ and $R^{11}$ groups that are especially useful for labelling target components with available sulphydryl functional groups include:

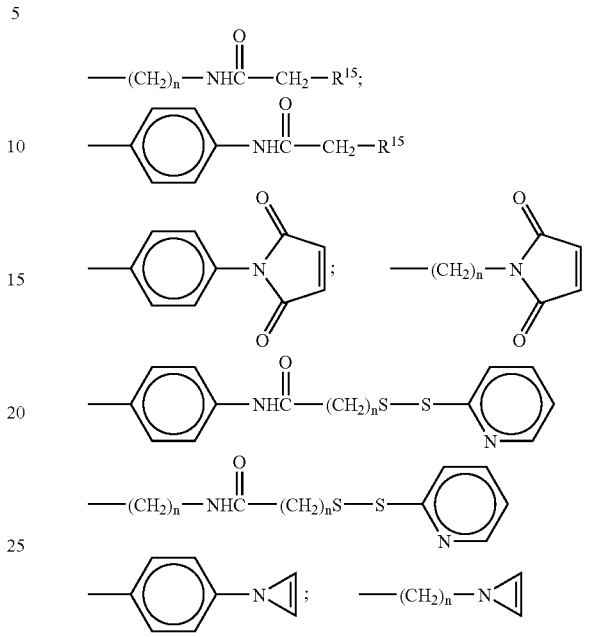

where n=0 or an integer from 1–10 and $R^{15}$ is a leaving group such as I or Br.

Specific examples of possible $R^1$–$R^9$ and $R^{11}$ functional groups that are especially useful for labelling target components by light-activated cross linking include:

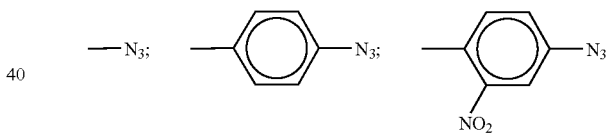

For the purpose of increasing water solubility or reducing unwanted non-specific binding of the fluorescently-labelled component to inappropriate components in the sample or to reduce interactions between two or more reactive chromophores on the labelled component which might lead to quenching of fluorescence, the $R^1$–$R^9$ and $R^{11}$ functional groups can be selected from the well known polar and electrically charged chemical groups. Examples of such groups are -E-F— where F is hydroxy, sulphonate, sulphate, carboxylate, substituted amino or quaternary amino, and where E is a spacer group such as —$(CH_2)_n$— where n is 0–6. Useful examples of -E-F groups include $C_{1-6}$ alkyl sulphonates, such as —$(CH_2)_3SO_3^-$ and —$(CH_2)_4$—$SO_3^-$.

Exemplary compounds of the present invention which demonstrate the capability for adjusting fluorescence colour, water solubility, and the position of the reactive or functional group are as follows:

i) 6,7,9,10-Tetrahydro-2,14-carboxymethyl-16,16,18,18-tetramethyl-7aH,8aH-bisindolinium[3,2-a;3'2'-a']pyrano[3,2-c;5,6-c']dipyridin-5-ium (Compound I);

ii) 8,9,11,12-Tetrahydro-3,17-disulphonato-20,20,22,22-tetramethyl-9aH,10aH-bisbenz[e]indolinium[3,2-a,3'2'-a']pyrano[3,2-c;5,6-c']dipyridin-7-ium (Compound II);

iii) 6,7,9,10-Tetrahydro-2-carboxymethyl-14-sulphonato-16,16,18,18-tetramethyl-7aH,8aH-bisindolinium[3,2-a,3'2'-a]pyrano[3,2-c;5,6-c']dipyridin-5-ium (Compound III);

iv) 6,7,9,10-Tetrahydro-2-carboxymethyl-14-sulphonato-16,16,18,18-tetramethyl-7aH,8aH-bisindolinium[3,2-a,3'2'-a]pyrano[3,2-c;5,6-c']dipyridin-5-ium, glycinamide (Compound IV);

v) 6,7,9,10-Tetrahydro-2-carboxymethyl-14-sulphonato-16,16,18,18-tetramethyl-7aH,8aH-bisindolinium[3,2-a,3'2'-a]pyrano[3,2-c;5,6-c']dipyridin-5-ium, N-(2-aminoethylcarboxamide) (Compound V);

vi) 6,7,9,10-Tetrahydro-2-(N-formyl)aminomethyl-14-sulphonato-16,16,18,18-tetramethyl-7aH,8aH-bisindolinium[3,2-a,3'2'-a]pyrano[3,2-c;5,6-c']dipyridin-5-ium (Compound VI);

vii) 6,7,9,10-Tetrahydro-2-hydroxyethyl-16,16,18,18-tetramethyl-7aH,8aH-bisindolinium[3,2-a,3'2'-a]pyrano[3,2-c;5,6-c']dipyridin-5-ium (Compound VII);

viii) 6,7,8,10-Tetrahydro-14-carboxymethyl-16,16-dimethyl-7a-8a-benzothiazolenine-indolenine-[3,2-a]-benzthiazolyl[3'2'-a]-pyrano[3,2-c;5,6-c']dipyridin-5-ium (Compound VIII);

ix) 6,7,8,8a,9,10-Hexahydro-2,14-disulphonato-8-(4-carboxy-anilino)-16,16,18,18-tetramethyl-7aH-bis-indolinium[3,2-a;3'2'-a']pyrido[3,2-c;5,6-c']dipyridin-5-ium (Compound IX);

x) 6,7,9,10-Tetrahydro-14-carboxymethyl-16,16-dimethyl-7a-8a-quinolino-indolenium-[3,2-a,3'2'-a]-pyrano[3,2-c;5,6-c']dipyridin-5-ium (Compound X).

The groups provided herein are not meant to be all-inclusive of those groups which can be incorporated at the R sites of the compounds of the present invention. It will be understood that there are various other groups which will react with groups on material that is to be labelled by the compounds of the present invention. Compounds produced by the incorporation of such other groups at the $R^1$–$R^9$ and $R^{11}$ positions are intended to be encompassed by the present invention.

The compounds of the present invention may be used in numerous biological and non-biological applications. With respect to non-biological applications, compounds of the present invention having one or more uncharged groups at the $R^1$–$R^9$ and $R^{11}$ positions, for example, $C_{1-26}$ alkyl and aryl moieties may be dissolved in non-polar materials to provide fluorescent properties to those materials. Such non-polar materials include, for example, paints, polymers, waxes, oils, inks and hydrocarbon solvents. Another non-biological application of the present invention is to dissolve compounds of the present invention having one or more charged and or polar groups at the $R^1$–$R^9$ and $R^{11}$ positions in polar solvents or other materials such as, for example, water, ethylene glycol, methyl alcohol, or a mixture of water and methyl alcohol. Such charged R-groups include, for example, —$NR_3^-$, —$SO_3^-$, —$PO_3^-$ and —$COO^-$, while such polar R-groups include, for example, hydroxyl groups. With respect to biological applications, biological molecules may be non-covalently labelled using the present complexes. For example, complexes of the present invention wherein at least one of $R^1$–$R^9$ and $R^{11}$ contains a charge, for example, quaternary amino, may be used to non-covalently bind to charged biological molecules such as, for example, DNA and RNA. In addition, compounds of the present invention wherein at least one of $R^1$–$R^9$ and $R^{11}$ is an uncharged group, for example, a long chain alkyl, may be used to bind to uncharged biological molecules such as, for example, biological lipids.

Alternatively, the compounds of the present invention may contain a polymerizable group suitable for the formation of a polymer containing the complex. Suitable polymerizable groups are selected from acrylate, methacrylate, acrylamide, vinyl and styryl. Polymerization may be carried out with a suitably derivatized compound of this invention used in conjunction with a second polymerizable monomer starting material, such as styrene or vinyltoluene, to form a copolymer containing the fluorescent compound. Alternatively the fluorescent compounds of the invention need not have a polymerisable group, for example, the compound may be incorporated during polymerisation or particle formation or may be absorbed into or onto polymer particles.

The dyes of the present invention can also be used as laser dyes according to the procedures set forth in U.S. Pat. No. 4,916,711 to Boyer and Morgan. Laser dyes must be fluorescent, must have a quantum yield greater than 0.56 or 0.57 and must be reasonably photostable. The compounds of the present invention satisfy each of these requirements. Further the dyes of the present invention can be used as textile dyes, photographic dyes and as organic conductors.

The compounds of the present invention may also be used to covalently label a target material to impart fluorescent properties to the target material. Covalent labelling using the compounds of the present invention may be utilized either in a biological or a non-biological application. Examples of target materials that may be labelled in non-biological applications include, for example, cellulose-based materials (including, for example, papers), textiles, petroleum-based products, photographic films, glasses, polymers and gel filtration and chromatography media.

Covalent labelling using compounds of the present invention may be accomplished with a target having at least one functional or reactive group as defined hereinbefore. The target may be incubated with an amount of a compound of the present invention having at least one of $R^1$–$R^9$ and $R^{11}$ that includes a reactive or functional group as hereinbefore defined that can covalently bind with the functional or reactive group of the target material. The target material and the compound of the present invention are incubated under conditions and for a period of time sufficient to permit the target material to covalently bond to the compound of the present invention.

$R^1$–$R^9$ and $R^{11}$ can be chosen so that the compounds of the present invention react with different target compounds and, or to have different spectral properties, thereby providing a number of related compounds which can be used in multiplex analyses wherein the presence and quantity of various compounds in a single sample must be differentiated based on the wavelengths and intensities of a number of detected fluorescence emissions.

The compounds of the present invention may be made soluble in aqueous, other polar, or non-polar media containing the material to be labelled by appropriate selection of R-groups.

The invention also relates to labelling methods wherein the compounds of the present invention including at least one reactive group at the $R^1$–$R^9$ and $R^{11}$ positions covalently react with amino, hydroxyl, aldehyde, phosphoryl, carboxyl, sulphydryl or other reactive groups on target materials. Such target materials are include, but are not limited to the group consisting of antibody, lipid, protein, peptide, carbohydrate, nucleotides which contain or are derivatized to contain one or more of an amino, sulphydryl, carbonyl, hydroxyl and carboxyl, phosphate and thiophosphate groups, and oxy or deoxy polynucleic acids which contain or are derivatized to contain one or more of an amino, sulphydryl, carbonyl, hydroxyl and carboxyl, phosphate and thiophosphate groups, microbial materials, drugs, toxins, particles, plastics or glass surfaces and polymers. Compounds of the present invention may also be used for coupling to additional fluorescent or non-fluorescent compounds for use in fluorescence resonance energy transfer complexes of the type described in EPA 747700 or for fluorescence polarisation or fluorescence quenching-based applications.

In addition to the foregoing single-step labelling process, the present invention also relates to two-step labelling processes in which, in a first step, a compound of the present invention covalently reacts with and thereby labels a primary component, such as an antibody. In a second or staining step of the two-step procedure, the fluorescently labelled primary component is then used as a probe for a secondary component, such as an antigen for which the antibody is specific. When the target of the so-labelled antibodies is a cell, the second step of the procedure may be used to determine the amount of labelled antibodies which are attached to that type of cell by determining the intensity of the fluorescence of the cells. By this two-step procedure, monoclonal antibodies and other components covalently labelled in the first step with the fluorescent compounds of the present invention could be used as antigen probes.

The compounds of the present invention can be used to determine the concentration of a particular protein or other component in a system. If the number of reactive groups on a protein which can react with a probe is known, the fluorescence per molecule can be known and the concentration of these molecules in the system can be determined by the total fluorescence intensity of the system. This particular method can be used to measure the concentration of various labelled analytes using microtitre plate readers or other known immunofluorescence detection systems.

The compounds of the present invention are also useful in assay methodologies that employ fluorescent labels for the detection and measurement of analytes, using for example, fluorescence resonance energy transfer (FRET) based methods, fluorescence lifetime, or by means of fluorescence polarization measurements.

The use of fluorescence resonance energy transfer dye pairs in biological systems is well known and they have been used in the detection of binding events or cleavage reactions in assays which employ FRET. Examples of such assays include equilibrium binding assays, (eg. immunoassays, nucleic acid hybridisation assays, protein binding assays and hormone receptor assays) and enzyme assays, such as proteolytic cleavage assays, the cleavage of a DNA or RNA molecule by a nuclease, or a lipid by a lipase.

Binding assays utilising compounds of the present invention may be performed by binding one component of a specific binding pair with a second component of the specific binding pair, the first component being labelled with a fluorescent donor dye according to the present invention, and the second component being labelled with a fluorescent (or quenching) acceptor dye, so as to bring about an energy transfer relationship between the first and second components, and detecting the binding of the first and second components by measurement of the emitted fluorescence. Examples of specific binding pairs include, but are not restricted to, antibodies/antigens, lectins/glycoproteins, biotin/(strept)avidin, hormone/receptor, enzyme/substrate or co-factor, DNA/DNA, DNA/RNA and DNA/binding protein. It is to be understood that in the present invention, any molecules which possess a specific binding affinity for each other may be employed, so that the dyes of the present invention may be used for labelling one component of a specific binding pair, which in turn may be used in the detection of binding to the other component.

The dyes of the present invention may also be used in an enzyme cleavage assay format, in which the enzyme substrate, for example a peptide, comprises two components, one of which is labelled with a fluorescent donor dye of the present invention, the second being labelled with a fluorescent (or quenching) acceptor dye and being attached to the substrate in an energy transfer relationship on either side of the substrate bond to be cleaved. A known or a putative enzyme inhibitor compound may be optionally included in the reaction mixture. Cleavage of the substrate by the enzyme results in separation of the donor and acceptor dyes, resulting in a loss of resonance energy transfer and a change in the fluorescence emission of the donor and acceptor species.

Suitable fluorescent acceptor dyes that can be combined with the dyes of the present invention to form energy transfer dye pairs include the rhodamine and cyanine dyes. Particularly preferred are the cyanine dyes, including Cy5 (1-($\epsilon$-carboxypentyl)-1'-ethyl-3,3,3',3'-tetramethyl-5,5'-disulphonato-dicarbocyanine), Cy5.5 (1-($\epsilon$-carboxypentyl)-1'-ethyl-3,3,3',3'-tetramethyl-4,5,4',5'-(1,3-disulphonato)-dibenzo-dicarbocyanine) and Cy7 (1-($\epsilon$-carboxypentyl)-1'-ethyl-3,3,3',3'-tetramethyl-5,5'-disulphonato-tricarbocyanine). A suitable quenching acceptor dye is DABCYL (4-(4-dimethylaminophenyl)azobenzoic acid).

The dyes of the present invention may also be used in binding assays or in enzyme cleavage assays, utilising fluorescence polarization measurements. In a binding assay format, the assay of an analyte in a sample may be performed by providing a specific binding partner for the analyte, the specific binding partner being labelled with a dye according to the present invention, measuring the fluorescence polarization of the labelled specific binding partner, contacting the analyte with the labelled specific binding partner under conditions suitable for binding the analyte to form an analyte-specific binding partner complex and measuring the fluorescence polarization of the labelled analyte-specific binding partner complex to determine the extent of binding.

In the second format, an assay for the detection of enzyme activity may be configured as follows. A reaction mixture is prepared by combining a protease enzyme and a fluorogenic substrate labelled with a dye according to the present invention. A known or a putative inhibitor compound may be optionally included in the reaction mixture. Cleavage of the substrate by the enzyme results in the production of labelled fragments. The progress of the reaction is monitored by observing the change in fluorescence polarization.

The fluorescent compounds of the present invention can also be used in a detection method wherein a plurality of the fluorescent compounds are covalently attached to a plurality of different primary components, such as antibodies, each primary component being specific for a different secondary component, such as an antigen, in order to identify each of a plurality of secondary components in a mixture of secondary components. According to this method of use, each of the primary components is separately labelled with a fluorescent compound having a different light absorption and emission wavelength characteristic compared with the dye molecules used for labelling the other primary components. The so-called primary components are then added to the preparation containing secondary components, such as antigens, and the primary components are allowed to attach to the respective secondary components for which they are selective.

Any unreacted probe materials may be removed from the preparation by, for example, washing, to prevent interference with the analysis. The preparation is then subjected to a range of excitation wavelengths including the absorption wavelengths of particular fluorescent compounds. A fluorescence microscope or other fluorescence detection system, such as a flow cytometer or fluorescence spectrophotometer, having filters or monochromters to select the rays of the excitation wavelength and to select the wavelengths of fluorescence is next employed to determined the intensity of the emission wavelengths corresponding to the fluorescent compounds utilized, the intensity of fluorescence indicating the quantity of the secondary component which has been bound with a particular labelled primary component. Known techniques for conducting multi-parameter fluorescence studies include, for example, multi-parameter flow cytometry.

In certain cases a single wavelength of excitation can be used to excite fluorescence from two or more materials in a mixture where each fluoresces at a different wavelength and the quantity of each labelled species can be measured by detecting its individual fluorescence intensity at its respective emission wavelength. If desired, a light absorption method can also be employed.

The detection method of the present invention can be applied to any system in which the creation of a fluorescent primary component is possible. For example, an appropriately reactive fluorescent compound can be conjugated to a DNA or RNA fragment and the resultant conjugate then caused to bind to a complementary target strand of DNA or RNA. Appropriate fluorescence detection equipment can then be employed to detect the presence of bound fluorescent conjugates.

The present invention also relates to the covalent reaction between compounds of the present invention, and amine, hydroxy, aldehyde, sulphydryl, phosphoryl or other known functional groups on materials such as, for example, proteins, peptides, carbohydrates, nucleic acids, derivatized nucleic acids, lipids, certain other biological molecules, biological cells, soluble polymers, polymeric particles, polymer surfaces, polymer membranes, glass surfaces and other particles and surfaces. Because detecting fluorescence involves highly sensitive optical techniques, the presence of these dye "labels" can be detected and quantitated even when the label is present in very low amounts. Thus, the dye labelling reagents can be used to measure the quantity of a material that has been labelled.

Compared with, for example, the fluoresceins, the rigidized trimethine cyanines of the present invention are particularly photostable and are insensitive to pH changes between pH2 and pH10. The compounds of the present invention maximally absorb and emit light at wavelengths between 450 and 600 nm (green to orange region of the spectrum) and are therefore alternatives to Texas-Red, rhodamine, tetramethylrhodamine, X-rhodamine, BODIPY and fluorescein.

The present invention also provides a process for the preparation of a compound of formula (2) which comprises treating a compound of formula (A):

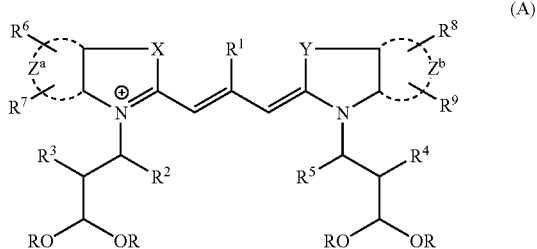

(A)

optionally substituted by groups $R^2$–$R^9$, wherein X, Y, $Z^a$, $Z^b$ and groups $R^1$, $R^2$, $R^3$, $R^4$, $R^5$, $R^6$, $R^7$, $R^8$ and $R^9$ are as defined above and R is methyl or ethyl, in mild acid solution, such as in acetic acid. Suitably the reaction mixture is heated under refluxing conditions, whereupon the rigidized carbocyanine dye precipitates from solution. Alternatively the reaction may be carried out in a stronger mineral acid solution, such a sulphuric acid at lower temperatures, for example ambient temperature. It may be advantageous to include in the reaction mixture, a solvent such as chloroform.

In the case of amino and hydrazino substituted carbocyanine dyes of the present invention, these may be prepared from intermediates of general structure (A) by including the appropriate amine or hydrazino derivative in the acid solution used for preparing the rigidized dye.

Symmetrical compounds of structure (A) wherein X and Y are the same and structures $Z^a$ and $Z^b$ are the same may be prepared by reacting a compound of structure (B):

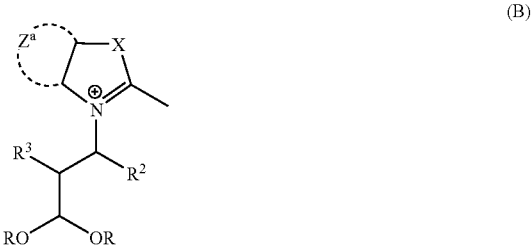

(B)

optionally substituted with groups $R^2$, $R^3$, $R^6$ and $R^7$ wherein groups, $Z^a$ and X, $R^2$, $R^3$, $R^6$ and $R^7$ are as hereinbefore defined and R is methyl or ethyl, with an appropriate ortho ester such a ethyl orthoformate in a suitable solvent medium to prepare the non-rigidized trimethine. The reaction is suitably carried out in solution in a solvent such as pyridine by heating under reflux. By suitably substituting the ortho ester, the central or meso carbon atom of the conjugated trimethine chain may be substituted with a variety of substituents such as are represented by the group $R^1$. For example, replacement of the ethyl orthoformate in the reaction mixture with ethyl orthoacetate will produce a trimethine cyanine dye in which the meso hydrogen is replaced with a methyl group.

Asymmetric compounds of structure (A) wherein X and Y are different may be prepared by reacting a compound of formula (B), optionally substituted with groups $R^5$ and $R^6$ wherein groups $R^2$, $R^3$, $R^5$, $R^6$, $Z^a$ and X are as hereinbefore defined with a compound of structure (C):

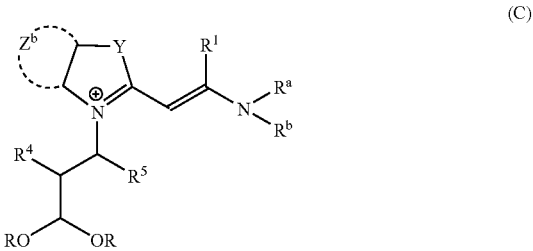

(C)

optionally substituted by groups $R^8$ and $R^9$ wherein groups $R^1$, $R^4$, $R^5$, $R^8$, $R^9$, Y and $Z^b$ are as hereinbefore defined, R is an alkyl group such as methyl or ethyl, $R^a$ is an acyl radical, such as acetyl, propionyl and benzoyl and $R^b$ is hydrogen, an alkyl radical such as methyl or ethyl, or an aryl radical such as phenyl. The reaction is suitably carried out in a 1:1 molar proportion in acetic anhydride solution.

Intermediate compound (B) may be prepared by reacting the hydrohalide acid salt of the appropriate heterocyclic base of formula (D):

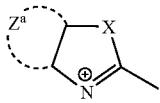

(D)

optionally substituted by groups $R^6$ and $R^7$, wherein X, $Z^a$, $R^6$ and $R^7$ are as defined above with a compound of formula (E):

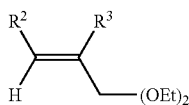

(E)

wherein $R^2$ and $R^3$ are as hereinbefore defined. The reaction is advantageously carried out with reagent (E) in excess and in an inert solvent of moderate polarity that dissolves both reagents, but which is not a solvent for the reaction product. Examples of such media are solvents such as acetonitrile. The reaction is suitably carried out at an elevated temperature, suitably 70° C. An acid such as acetic acid may be added to the reaction mixture to facilitate the reaction. As a specific example the hydrobromide salt of (2,3,3-trimethyl-3H-indol-5-yl)-acetic acid prepared by the method of Southwick et al (Org. Prep. Proceed. Int. 20, 279–84, 1989) is reacted with acrolein diethyl acetal in acetonitrile containing acetic acid as solvent. The reaction is suitably carried out at a temperature of 70° C.

Intermediates of formula (C) may be prepared by reaction of a compound of structure (B) containing a methyl substituent in the 2-position with a formamidine of formula (F):

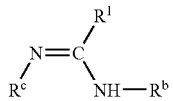

(F)

wherein $R^1$ and $R^b$ are as hereinbefore defined and $R^c$ is phenyl or substituted phenyl. Suitably the reaction is carried out by condensing the quaternary salt of structure (B) with a 1.5 molar excess of the formamidine using an acid condensing agent, for example acetic anhydride, propionic anhydride, or glacial acetic acid. Acetic anhydride is a particularly preferred condensing agent for the reaction. Alternatively, the condensation reaction may be performed without any addition; however acid condensation is to be preferred for the production of rigidized trimethine cyanine dyes substituted at the central or meso carbon atom of the trimethine chain. See, for example, British Patent No. 412309.

Precursor compounds of formula such as (D) may be prepared by methods well known to those skilled in the area. See for example U.S. Pat. No. 4,981,977, the entire disclosure of which is incorporated by reference.

It will be readily appreciated that certain compounds of formula (2) may be useful as intermediates for conversion to other compounds of the formula (2) by methods well known to those skilled in the art. Likewise, certain of the intermediates may be useful for the synthesis of derivatives of formula (2). The compounds of the present invention may be synthesized by the methods disclosed herein. Derivatives of the compounds having a particular utility are prepared either by selecting appropriate precursors or by modifying the resultant compounds by known methods to include functional groups at a variety of positions. As examples, the complexes of the present invention may be modified to include certain reactive groups for preparing a fluorescent labelling reagent, or charged or polar groups may be added to enhance the solubility of the compound in polar or nonpolar solvents or materials. As examples of conversions an ester may be converted to a carboxylic acid or may be converted to an amido derivative.

The following are specific examples of the synthesis of compounds of the present invention and observed spectral data for those compounds.

EXAMPLE 1

6,7,9,10-Tetrahydro-2,14-carboxymethyl-16,16,18,18-tetramethyl-7aH,8aH-bisindolinium[3,2-a;3'2'-a'] pyrano[3,2-c;5,6-c']dipyridin-5-ium (R-Cy3.12.OH; Compound I)

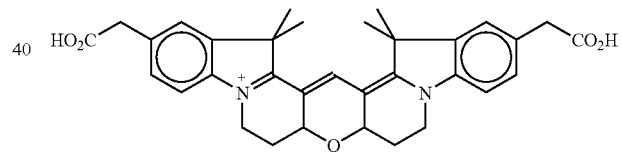

1.1 5-Carboxymethyl-2,3,3-trimethylindoline

5-Carboxymethyl-2,3,3-trimethylindoline was prepared either by the method of Southwick et al, Org. Prep. Proceed. Int., 20, 274–84, (1989), or alternatively as described below.

To a stirred solution of 4-aminophenylacetic acid (5 g, 33.1 mmol) in a 3:2 water: conc. HCl (33 ml) solvent mixture at <0° C. was added dropwise a cooled (<0° C.) solution of sodium nitrite (2.7 g, 39 mmol) in water (43 ml). The reaction mixture was then maintained at the reduced temperature for a further 30 minutes. A saturated aqueous solution of sulphur dioxide (140 ml) was added and the reaction mixture warmed to ambient temperature over 1 hour, then warmed for a further hour at 70° C. The reaction mixture was cooled rapidly and the solvent removed in vacuo. The yellow hydrazine intermediate product obtained was redissolved in acetic acid (54 ml) and potassium acetate (7.05 g, 71.8 mmol) and methyl-isopropyl ketone (6.84 g, 79.4 mmol) added at ambient temperature. After 30 minutes the reaction mixture was warmed to 90° C. and stirred for a further 2 hours. The reaction mixture was cooled and the reaction solvent removed in vacuo. The product was dissolved in dichloromethane (100 ml) and washed with water (2×50 ml). The organic phase was dried over MgSO$_4$, filtered and concentrated in vacuo. 5-ethoxycarbonyl-2,3,3-trimethylindolenine was obtained as a red solid (4.8 g, 67%). No purification was required; m/z (Maldi): 217.

1.2 1-(3,3-Diethoxypropyl-5-carboxymethyl-2,3,3-trimethylindolenine, ethyl ester To a stirred solution of 5-carboxymethyl-2,3,3-trimethylindolenine (2 g, 9.3 mmol) in ethanol (40 ml) at ambient temperature was added hydrobromic acid (3.16 ml of 48% aqueous solution). After 1 hour the reaction solvent was removed in vacuo. The hydrobromide salt was redissolved in acetonitrile (40 ml) and acetic acid (400 ml) and acrolein diethyl acetal (18.17 g, 140 mmol) added. The reaction mixture was warmed to 70° C. for 20 minutes. The solution was cooled and the reaction solvent removed in vacuo. The product was purified by HPLC on a Rainin Dynamax C18, 8 μm column using a 10–100% gradient elution of water/acetonitrile (containing 0.1% TFA) over 60 minutes at 20 ml/min. The product was obtained as a green oil (1.24 g, 36%); m/z (FAB$^-$): 376.2.

1.3 5,5'-Dicarboxymethyl-1,1'-di-(3,3-diethoxypropyl)-indocarbocyanine-ethyl ester To a stirred solution of 1-(3,3-diethoxypropyl-5-carboxymethyl-2,3,3-trimethylindolenine, ethyl ester (356 mg, 0.95 mmol) in pyridine (10 ml) at 120° C. was added dropwise, triethyl orthoformate (98 mg, 66 mmol) over 30 minutes. After 2 hours the reaction mixture was cooled. The product was purified by HPLC on a Rainin Dynamax C18, 8 μm column using a 10–100% gradient elution of water/acetonitrile (containing 0.1% TFA) over 60 minutes at 20 ml/min. The product was obtained as a pink solid (251 mg, 35%); λmax: 555 nm; m/z (FAB$^-$): 761.4.

1.4 6,7,9,10-Tetrahydro-2,14-carboxymethyl-16,16,18,18-tetramethyl-7aH,8aH-bisindolinium[3,2-a,3'2'-a]pyrano[3,2-c;5,6-c']dipyridin-5-ium To a stirred solution of 5,5'-carboxymethyl-1,1-di-(3,3-diethoxypropyl)-indocarbocyanine, ethyl ester (100 mg, 0.132 mmol) in chloroform (10 ml) at ambient temperature was added 50% aqueous sulphuric acid (2 ml). After 30 minutes the reaction solvent was diluted with chloroform (10 ml) and washed with water (3×10 ml). The organic phase was dried over NaSO$_4$, filtered and concentrated in vacuo. The product was purified by HPLC on a Rainin Dynamax C18, 8 μm column using a 10–100% gradient elution of water/acetonitrile (containing 0.1% TFA) over 60 minutes at 20 ml/min. The product was obtained as a pink solid (65 mg, 90%); λmax 565 nm; m/z; m/z (FAB$^-$): 539.2.

1.5 6,7,9,10-Tetrahydro-2,14-carboxymethyl-16,16,18,18-tetramethyl-7aH,8aH-bisindolinium[3,2-a,3'2'-a]pyrano[3,2-c;5,6-c']dipyridin-5-ium, N-hydroxysuccinmidyl ester To a mixture of O—(N-succinimidyl-N,N,N',N'-bis(tetramethylene)uronium hexafluorophosphate (5 mg, 0.012 mmol), and N,N'-diisopropylethylamine (4.08 mg, 0.032 mmol) in dimethylsulphoxide (500 μl) at ambient temperature was added 6,7,9,10-tetra-2,14-carboxymethyl-16,16,18, 18-tetramethyl-7aH,8aH-bisindolinium[3,2-a,3'2'-a]pyrano[3,2-c;5,6-c']dipyridin-5-ium (5 mg, 0.0089 mmol). The reaction mixture was stirred for 1 hr. Conversion to the N-hydroxysuccinimidyl ester derivative was confirmed by mass Spectroscopy and HPLC using a Phenomenex Jupiter C18 10 μm column.

1.6 Protein Labelling Procedure

A stock solution of the N-hydroxysuccinimidyl ester of Compound I was prepared in dry DMF (1 mg active ester/100 μl ). Sheep IgG (1 mg, 6.45 mmol) was dissolved in 250 μl buffer solution (pH 9.4) and the desired amount of dye was added during vigorous vortex mixing. Unconjugated dye was separated from the labelled protein by gel permeation chromatography (0.7×20 cm column of Sephadex G-50) using pH 7 buffer solution as eluant. Absorption spectra of the labelled antibody solution was recorded (see FIG. 1). Dye to protein ratio for the sample was determined using an equation below with measured values of absorbance of the labelled dye at 560 nm and the absorbance of protein at 280 nm.

$$\frac{D}{P} = \frac{A_{dye} \times E_{prot}}{(A_{280} - X A_{dye}) \times E_{dye}}$$

The factor X in the denominator accounts for the dye absorption at 280 nm which is a % of the absorption of the dye at its maximum absorption ($A_{dye}$). The value of X is 0.17 for a rigid dye.

1.7 Comparison of Spectral Properties: Rigidized Cy3 (Compound I) and Open Chain Cy3

Figure 3:
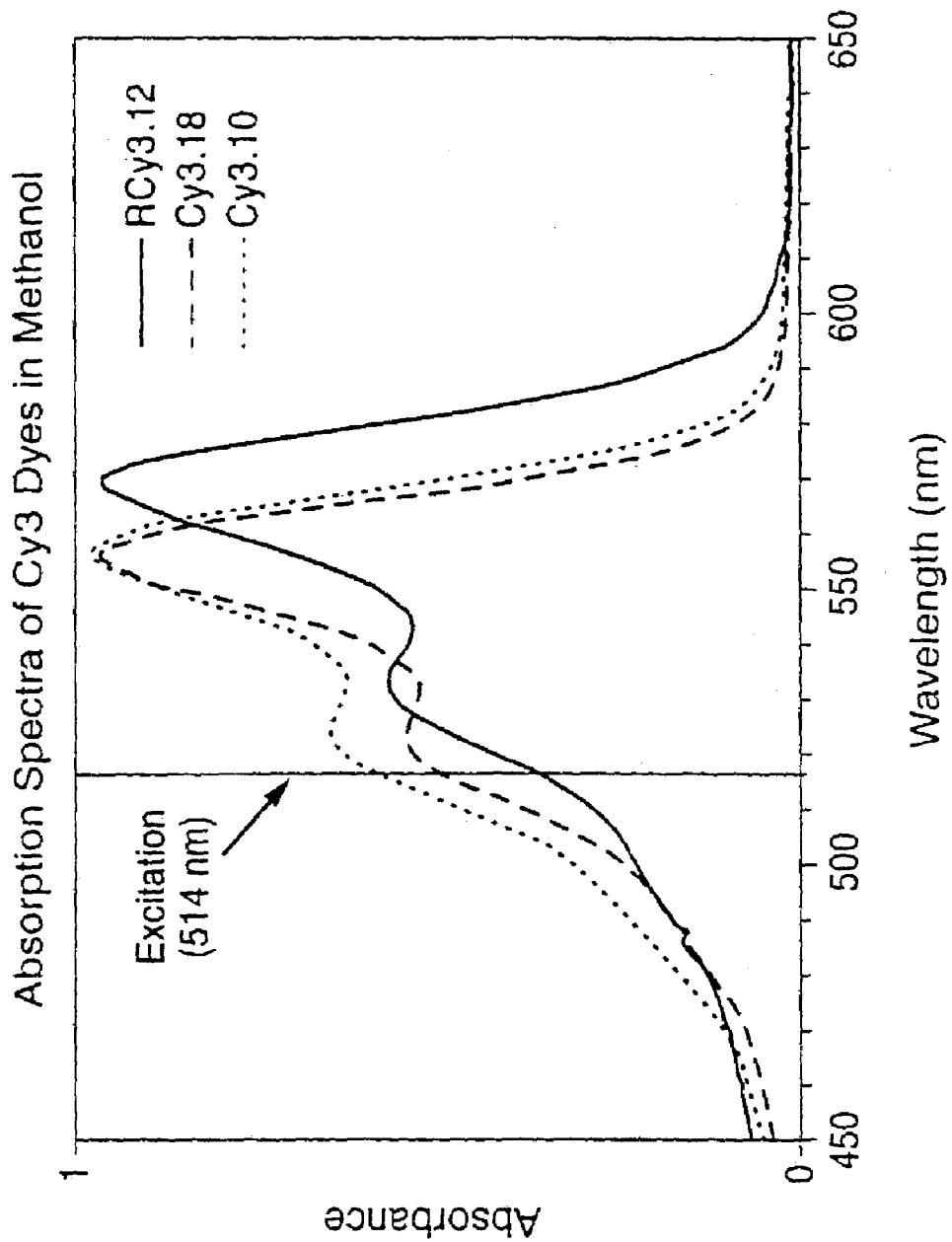
FIG. 3 is a graph comparing the spectral properties of the three cyanine 3 dyes of FIG. 2.
Figure 4:
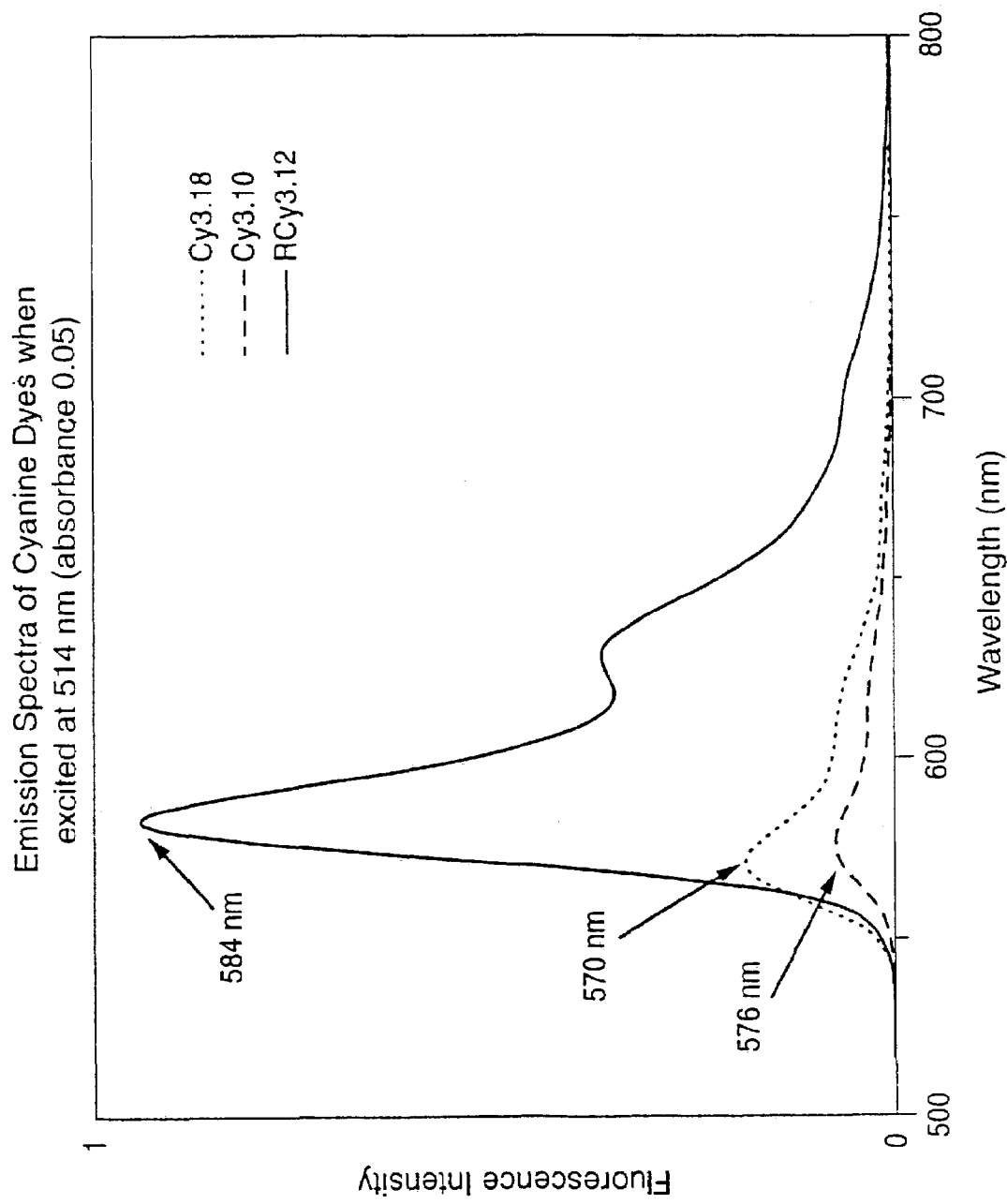
FIG. 4 is a graph showing the emission spectra of the three cyanine dyes of FIG. 2 when excited at 514 nm.

The spectral properties of the rigidized dye were compared with the known open chain Cy3.18.OH and Cy3.10.OH dyes (FIG. 2). The absorption absorption and emission spectra are shown in FIGS. 3 and 4. The absorption maxima of the rigid dye shifted to the red by 12 nm in methanol and as expected it is 10–12 time brighter that the non-rigidized indocyanines. The results are shown in Table 2 below.

TABLE 2

| Dye in Methanol | $\lambda_{max}$ | $\epsilon_{max}$ | QY (φ) |
|---|---|---|---|
| R-Cy3.12.OH (Compound I) | 565 | 584 | 0.8 |
| Cy3.18.OH | 555 | 570 | 0.09 |
| Cy3.10.OH | 555 | 578 | 0.08 |

Figure 5:
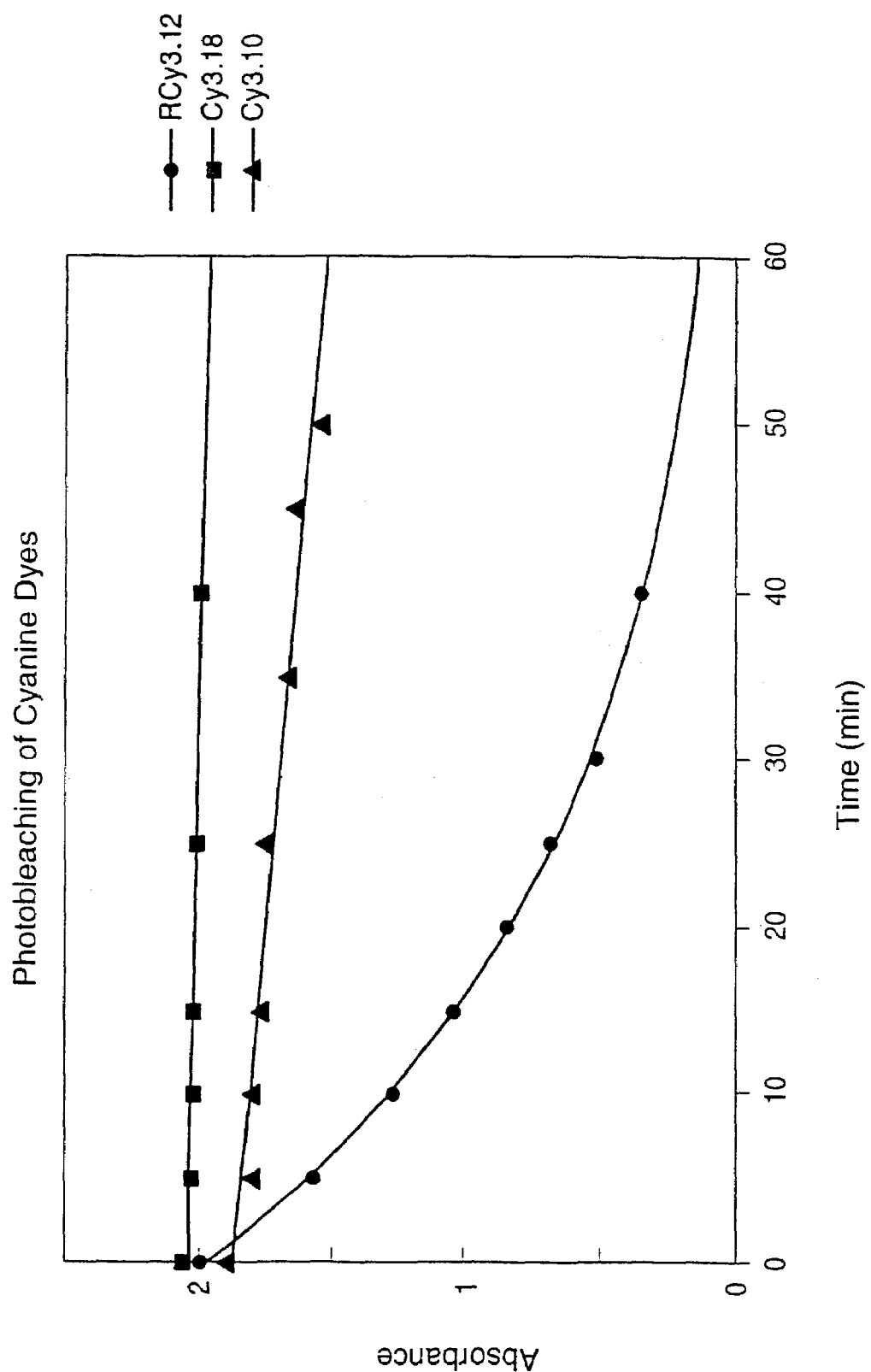
FIG. 5 shows the results of photo bleaching the three dyes of FIG. 2 when exposed to laser.

Photo-bleaching of the dyes was studied under identical conditions. Samples of equal concentrations of dyes (3 ml of 1.5×10$^{-5}$ mmol solution in water) were exposed to a laser line 514 nm (30 mV, 1 cm diam. beam) and absorption was recorded in a few minutes of interval for 50 minutes. The results are shown in FIG. 5. Rigidized dye is expected to bleach faster. However, because of its high quantum yield, it is expected that the rigidized dye will be suitable for flow cytometer and other imaging experiments where the sample is exposed for short time periods.

EXAMPLE 2

8,9,11,12-Tetrahydro-3,17-disulphonato-20,20,22,22-tetramethyl-9aH,10aH-bisbenz[e]indolinium[3,2-a,3'2'-a]pyrano[3,2-c;5,6-c']dipyridin-7-ium (Compound II)

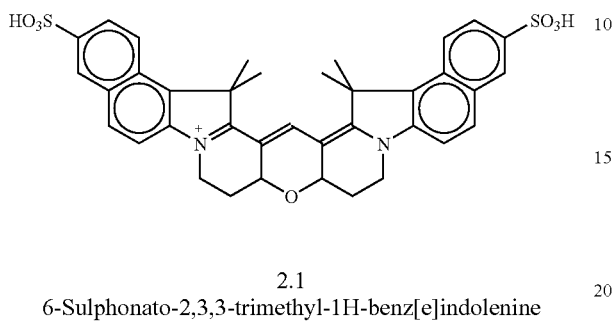

2.1 6-Sulphonato-2,3,3-trimethyl-1H-benz[e]indolenine

A stirred solution of 2,3,3-trimethyl-1H-benz[e]-indolenine (100 g, 478 mmol) in concentrated sulphuric acid (500 ml) was heated at 180° C. After 2 hours the solution was cooled to ambient temperature, then poured onto ice. The reaction mixture was made basic by adding 50% sodium hydroxide (3000 ml). The resulting precipitate was filtered, recrystallised from water and dried The product was obtained as a white solid (7.259, 54%).

2.2 1-(3,3-Diethoxypropyl)-6-sulphonato-2,3,3-trimethyl-1H-benz[e]indolenine 1-(3,3-Diethoxypropyl)-6-sulphonato-2,3,3-trimethyl-1H-benz[e]indolenine was prepared by reaction of 6-sulphonato-2,3,3-trimethyl-1H-benz[e]indolenine (25 mg, 0.0087 mmol) with acrolein diethyl acetal (169 mg, 1.3 mmol) and acetic acid (10 μl) in acetonitrile (2 ml) by an analogous method to that described in Section 1.2. The compound was not purified, as decomposition was observed. The product was obtained as a pale yellow oil.

2.3 6,6'-Disulphonato-1,1'-di-(3,3-diethoxypropyl)-benz[e]indo-carbocyanine 6,6'-Disulphonato-1,1-di-(3,3-diethoxypropyl)-benz[e]indocarbocyanine was prepared by reaction of 1-(3,3-diethoxypropyl)-6-sulphonato-2,3,3-trimethyl-1H-benz[e]indolenine with triethyl orthoformate (51.2 mg, 0.035 mmol) in pyridine (5 ml) by an analogous method to that described in Section 1.3. The compound was purified by HPLC on a Phenomenex Jupiter C18, 10 μm column using 0–100% gradient elution of water/acetonitrile (containing 0.1% TFA) over 30 minutes at 4 ml/min. The product was obtained as a pink/purple solid; λmax (MeOH) 580 nm, m/z (Maldi): 852.

2.4 8,9,11,12-Tetrahydro-3,17-disulphonato-20,20,22,22-tetramethyl-9aH,10aH-bisbenz[e]indolinium[3,2-a,3'2'-a]pyrano[3,2-c;5,6-c']dipyridin-7-ium 8,9,11,12-Tetrahydro-3,17-disulphonato-20,20,22,22-tetramethyl-9aH,10aH-bisbenz[e]indolinium[3,2-a,3'2'-a]pyrano[3,2-c;5,6-c']dipyridin-7-ium was prepared by reaction of 6,6'-disulphonato-1,1-di-(3,3-diethoxypropyl)-benz[e]indocarbocyanine (3 mg, 0.0035 mmol) in chloroform (5 ml) and 50% sulphuric acid (1 ml) by an analogous method to that described in section 1.4.

The compound was purified by HPLC on a Phenomenex Jupiter C18, 10 μm column using 0–100% gradient elution of water/acetonitrile (containing 0.1% TFA) over 30 minutes at 4 ml/min. The product was obtained as a luminescent pink/purple solid; λmax (MeOH) 598 nm; m/z (Maldi): 684.

EXAMPLE 3

6,7,9,10-Tetrahydro-2-carboxymethyl-14-sulphonato-16,16,18,18-tetramethyl-7aH,8aH-bisindolinium[3,2-a,3'2'-a]pyrano[3,2-c;5,6-c']dipyridin-5-ium (Compound III)

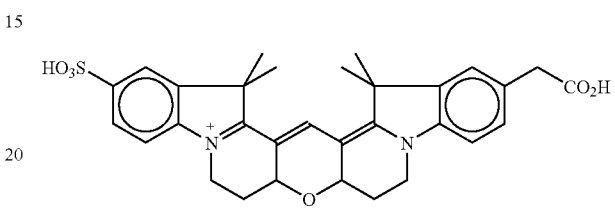

3.1 5-Sulphonato-2,3,3-trimethylindolenine

To a stirred solution of 4-hydrazinobenzene sulphonic acid (68 g, 361 mmol) in acetic acid (205 ml) at ambient temperature was added 3-methyl-2-butanone (88.44 g, 1027 mmol). The reaction was heated under reflux. After 3 hours the solution was cooled and the resulting pink precipitate was filtered, washed with acetic acid (50 ml) and dried. The product was redissolved in methanol (800 ml) and a solution of potassium hydroxide (20.4 g, 364 mmol) in isopropanol (200 ml) was added. The yellow solid obtained was filtered and dried (48 g, 56%); m/z (FAB$^+$): 240.

3.2 1-(3,3-Diethoxypropyl)-5-sulphonato-2,3,3-trimethylindolenine

1-Diethoxy propyl-5-sulphonato-2,3,3-trimethylindolenine was prepared by reaction of 5-sulphonato-2,3,3-trimethylindolenine potassium salt (1 g, 3.88 mmol) with acrolein diethyl acetal (8.54 g, 65.6 mmol) and acetic acid (1 ml) in acetonitrile (40 ml) using an analogous method to that described in Section 1.2. The compound was purified by HPLC on a Rainin Dynamax C18, 8 μm column using 0–100% gradient elution of water/acetonitrile (containing 0.1% TFA) over 60 minutes at 20 ml/min. The product was obtained as a green oil (740 mg, 52%); m/z: (FAB$^+$) 370.1.

3.3 5-Carboxymethyl-1-(3,3-diethoxypropyl)-2-(2-N-acetyl-N-phenylamino)ethenyl-2,3,3-trimethylindolenine To a stirred solution of 5-carboxymethyl-1-(3,3-diethoxypropyl)-2,3,3-trimethylindolenine-ethyl ester (1.16 g, 3.09 mmol) in acetic anhydride (25 ml) was added N,N'-diphenylformamidine (908 mg, 4.63 mmol). The reaction mixture was warmed to 110° C. After 30 minutes the solution was cooled and the reaction solvent removed in vacuo. The product was purified by HPLC on a Rainin Dynamax C18, 8 μm column using 10–100% gradient elution of water/acetonitrile (containing 0.1% TFA) over 60 minutes at 20 ml/min. The product was obtained as a pale brown oil (634 mg, 40%); m/z (FAB$^+$): 521.2.

3.4 5-Carboxymethyl-5'sulphonato-1,1'-di-(3,3-diethoxyoropyl)-indocarbocyanine, ethyl ester To a stirred solution of 5-carboxymethyl-1-(3,3-diethoxypropyl)-2-(2-N-acetyl-N-phenylamino)ethenyl-2,3,3-trimethylindolenine (96 mg, 0.19 mmol ) in 4.5:4.5:1 pyridine:acetic acid:acetic anhydride (5 ml) at ambient temperature was added a solution of 5-sulphonato-1-(3,3-diethoxypropyl)-2,3,3-trimethylindolenine (67.7 mg, 0.19 mmol) in 4.5:4.5:1 pyridine:acetic acid:acetic anhydride (5 ml). The reaction mixture was warmed to 70° C. for 5 hours. The solution was cooled and the reaction solvent removed in vacuo. The product was purified by HPLC on a Rainin Dynamax C18, 8 μm column using a 10–100% gradient elution of water/acetonitrile (containing 0.1% TFA) over 60 minutes at 20 ml/min. The product was obtained as a pink solid (33 mg, 24%); λmax (MeOH) 555 nm; m/z (FAB$^+$): 755.3.

3.5 6,7,9,10-Tetrahydro-2-carboxymethyl-14-sulphonato-16,16,18,18-tetramethyl-7aH,8aH-bisindolinium[3,2-a,3'2'-a]pyrano[3,2-c;5 6-c']dipyridin-5-ium 6,7,9,10-Tetrahydro-2-carboxymethyl-14-sulphonato-16,16,18,18-tetramethyl-7aH,8aH-bisindolinium[3,2-a,3'2'-a]pyrano[3,2-c;5,6-c']dipyridin-5-ium was prepared by reaction of 5-carboxymethyl-5'sulphonato-1-di-(3,3-diethoxypropyl)-indocarbocyanine, ethyl ester (33 mg, 0.044 mmol) in chloroform (10 ml) and 50% sulphuric acid (2 ml) by an analogous method to that described in Section 1.4. The product was purified by HPLC on a Rainin Dynamax C18 column using a 0–100% gradient elution of water/acetonitrile (containing 0.1% TFA) over 60 minutes at 20 ml/min. The product was obtained as a pink solid (18.7 mg, 76%); λmax (MeOH) 563 nm; m/z (FAB$^+$): 561.

3.6 6,7,9,10-Tetrahydro-2-carboxymethyl-14-sulphonato-16,16,18,18-tetramethyl-7a H,8aH-bisindolinium[3,2-a,3'2'-a]pyrano[3,2-c;5,6-c']dipyridin-5-ium, N-hydroxysuccinimidyl ester To a mixture of O—(N-succinimidyl-N,N,N',N'-bis(tetramethylene)uronium hexafluorophosphate (5 mg, 0.012 mmol), and N,N'-diisopropylethylamine (4.08 mg, 0.032 mmol) in dimethyl sulphoxide (500 μl) at ambient temperature was added 6,7,9,10-tetrahydro-2-carboxymethyl-14-sulphonato-16,16,18,18-tetramethyl-7aH,8aH-bisindolinium[3,2-a,3'2'-a]pyrano[3,2-c;5,6-c']dipyridin-5-ium(5 mg, 0.0089 mmol). The reaction was stirred for 1 hr. Conversion to the N-hydroxysuccinimidyl ester derivative was confirmed by mass spectroscopy and HPLC using a Phenomenex Jupiter $C_{18}$ 10 μm column.

EXAMPLE 4

6,7,9,10-Tetrahydro-2-carboxymethyl-14-sulphonato-16,16,18,18-tetramethyl-7aH,8aH-bisindolinium[3,2-a,3'2'-a]pyrano[3,2-c;5,6-c']dipyridin-5-ium, glycinamide (Compound IV)

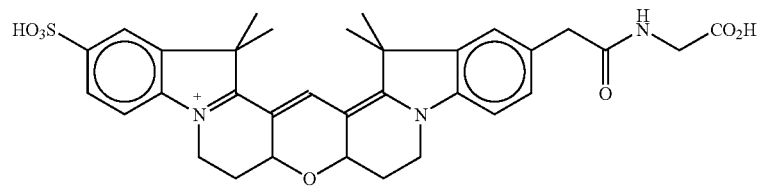

To a mixture of O—(N-succinimidyl-N,N,N',N'-bis(tetramethylene)uronium hexafluorophosphate (1 mg, 0.0024 mmol) and N,N'-diisopropylethylamine (0.82 mg, 0.0032 mmol) in dimethylformamide (100 ml) at ambient temperature was added 6,7,9,10-tetrahydro-2-carboxymethyl-14-sulphonato-16,16,18,18-tetramethyl-7aH,8aH-bisindolinium [3,2-a,3'2'-a]pyrano[3,2-c;5,6-c']dipyridin-5-ium (1 mg, 0.0018 mmol). After 1 hour, glycine (0.2 mg, 0.0027 mmol) was added and the solution stirred for a further 3 hours. The product was purified by HPLC on a Phenomenex Jupiter $C_{18, 10}$ μm column, using 0–100% gradient elution of water/acetonitrile (containing 0.1% TFA) at 4 ml/min. The product was obtained as a pink solid (0.22 mg, 30%); m/z (Maldi): 618.

EXAMPLE 5

6,7,9,10-Tetrahydro-2-carboxymethyl-14-sulphonato-16,16,18,18-tetramethyl-7aH,8aH-bisindolinium[3,2-a,3'2'-a]pyrano[3,2-c;5,6-c']dipyridin-5-ium, N-(2-aminoethylcarboxamide) (Compound V)

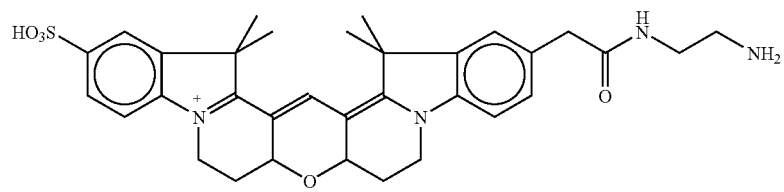

To a mixture of O—(N-succinimidyl-N,N,N',N'-bis(tetramethylene)uronium hexafluorophosphate (5 mg, 0.012 mmol) and N,N'-diisopropylethylamine (4.08 mg, 0.032 mmol) in dimethylformamide (500 ml) at ambient temperature was added 6,7,9,10-tetrahydro-2-carboxymethyl-14-sulphonato-16,16,18,18-tetramethyl-7aH,8aH-bisindolinium [3,2-a,3'2'-a]pyrano[3,2-c;5,6-c']dipyridin-5-ium (5 mg, 0.0089 mmol). After 1 hour tert-butyl-N-(2-aminoethyl)-carbamate (1.4 mg, 0.0089 mmol) was added and the solution stirred for a further 2 hours. The solvent was removed in vacuo. The product was dissolved in a 95% aqueous trifluoroacetic acid solution and stirred for 2 hours. The product was purified by HPLC on a Phenomenex Jupiter C18, 10 μm column, using gradient elution of acetonitrile/water (containing 0.1% TFA). The product was obtained as a pink solid (1.6 mg, 30%); m/z (FAB$^-$): 603.1.

EXAMPLE 6

6,7,9,10-Tetrahydro-2-(N-formyl)aminomethyl-14-sulphonato-16,16,18,18-tetramethyl-7aH,8aH-bisindolinium[3,2-a,3'2'-a]pyrano[3,2-c;5,6-c']dipyridin-5-ium (Compound VI)

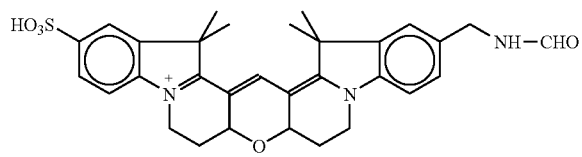

6.1 5-Phthalimidomethyl-2,3,3-trimethylindolenine

To a stirred solution of 2,3,3,-trimethylindolenine (20 g, 126 mmol) in concentrated sulphuric acid (100 ml) at ambient temperature was added portionwise N-hydroxymethylphthalimide (20 g, 114 mmol). After 70 hours the reaction mixture was poured onto ice and made basic with concentrated ammonium hydroxide. The resulting precipitate was filtered and dried. The product was obtained as a yellow solid (34.84 g, 87%).

6.2 5-Aminomethyl-2,3,3-trimethylindolenine

To a stirred solution of 5-phthalimidomethyl-2,3,3-trimethylindolenine (10 g, 31.4 mmol) in methanol (50 ml) at ambient temperature was added hydrazine hydrate (13.1 g 409 mmol). After 20 hours a precipitate was formed. The reaction mixture was adjusted to pH 1 with 6N HCl and the solvent removed in vacuo. The solid obtained was suspended in 1N HCl and filtered through celite. The filtrate was washed with dichloromethane (3×40 ml) and the aqueous phase adjusted to pH 12 with 6N NaOH, then extracted with dichloromethane (3×40 ml). The organic phase was dried over Na$_2$SO$_4$, filtered and concentrated in vacuo to give a pale yellow solid (4.98 g, 84%); m/z (Maldi): 188.

6.3 5-(N-Formyl)aminomethyl-2,3,3-trimethylindolenine

A stirred solution of 5-aminomethyl-2,3,3-trimethylindolenine (4.98 g, 26.5 mmol) in methyl formate (30 ml) was refluxed under a nitrogen atmosphere for 22 hours. The solution was cooled and the solvent removed in vacuo. The product was obtained as pale brown oil (5.4 g, 94%); m/z (FAB$^-$): 217.1.

6.4 1-(3,3-Diethoxypropyl)-5-(N-formylaminomethyl-2,3,3-trimethylindolenine 1-(3,3'-Diethoxypropyl)-5-(N-formyl)aminomethyl-2,3, 3-trimethylindolenine was prepared by reaction of 5-(N-formyl)aminomethyl-2,3,3-trimethylindolenine (1 mg, 24.8 mmol) with acrolein diethyl acetal (9 g, 69.1 mmol) and acetic acid (1 ml) in acetonitrile (40 ml) by an analogous method to that described in Section 1.2. The product was purified by HPLC no on a Rainin Dynamax C18, 8 μm column using a 0–100% gradient elution of water/acetonitrile (containing 0.1% TFA) over 60 minutes at 20 ml/min The product was obtained as a yellow oil (1.10 mg, 69%); m/z (Maldi): 347.

6.5 1-(3,3-Diethoxypropyl)-2-(2-N-acetyl-N-phenylamino)ethenyl-5-sulphonato-2,3,3-trimethylindolenine 1-(3,3-Diethoxypropyl)-2-(2-N-acetyl-N-phenylamino) ethenyl-5-sulphonato-2,3,3-trimethylindolenine was prepared by reaction of 5-sulphonato-1-(3,3'-diethoxypropyl)-2, 3,3-trimethylindolenine (100 mg, 0.27 mmol) [prepared as described in Section 3.2] with N,N'-diphenylformamidine (79 mg, 0.405 mmol) in acetic anhydride (20 ml) by an analogous method to that described in Section 3.3. The product was not purified, as decomposition was observed. The product was obtained as a yellow oil.

6.6 1,1-Di-(3,3'-diethoxypropyl)-5-(N-formyl)aminomethyl-5'-sulphonato-indocarbocyanine To a stirred solution of 5-sulphonato-1-(3,3-diethoxypropyl)-2-(2-N-acetyl-N-phenylamino)ethenyl-2,3,3-trimethylindolenine(37 mg, 0.072 mmol) in 4.5:4.5:1 pyridine:acetic acid:acetic anhydride (5 ml) at ambient temperature was added a solution of 1-(3,3-diethoxypropyl)-5(N-formyl)aminomethyl-2,3,3-trimethylindolenine (25 mg, 0.072 mmol) in 4.5:4.5:1 pyridine:acetic acid:acetic anhydride (5 ml). The reaction mixture was warmed to 70° C. for 5 hours. The solution was cooled and the solvent removed in vacuo. The product was purified by HPLC on a Rainin dynamax C18, 8 μm column using a 10–100% gradient elution of water/acetonitrile (containing 0.1% TFA) over 60 minutes at 20 ml/min. The product was obtained as a pink solid (16 mg, 15%); λmax (MeOH); 555 nm, m/z (FAB$^-$): 726.1.

6.7 6,7,9,10-Tetrahydro-2-(N-formyl)aminomethyl-14-sulphonato-16,16,18,18-tetramethyl-7aH,8aH-bisindolinium[3,2-a,3'2'-a]pyrano[3,2-c;5,6-c']dipyridin-5-ium 6,7,9,10-Tetrahydro-2-(N-formyl)aminomethyl-14-sulphonato-16,16,18,18-tetramethyl-7aH,8aH-bisindolinium[3,2-a,3'2'-a]pyrano[3,2-c;5,6-c']dipyridin-5-ium was prepared by reaction of 1,1-Di-(3,3-diethoxypropyl)-5-(N-formyl)aminomethyl-5'-sulphonato-indocarbocyanine (5 mg, 0.0069 mmol) in chloroform (5 ml) and 50% sulphuric acid (1 ml) by an analogous method to that described in Section 1.4. The product was purified by HPLC on a Rainin Dynamax C18, 8 μm column using a 0–100% gradient elution of water/acetonitrile (containing 0.1% TFA) over 60 minutes at 20 ml/min. The product was obtained as a pink solid (3.3 mg, 90%); λmax (MeOH) 564 nm; m/z (Maldi): 560.

6.8 6,7,9,10-Tetrahydro-2-aminomethyl-14-sulphonato-16,16,18,18-tetramethyl-7aH,8aH-bisindolinium[3,2-a,3'2'-a]pyrano[3,2-c;5,6-c']dipyridin-5-ium A solution of 6,7,9,10-tetrahydro-2-(N-formyl)aminomethyl-14-sulphonato-16,16,18,18-tetramethyl-7aH,8aH-bisindolinium[3,2-a,3'2'-a]pyrano[3,2-c;5,6-c']dipyridin-5-ium (2 mg) in conc. HCl: methanol [1:12] (5 ml) was stirred for 12 hours. The reaction solvent was removed in vacuo and the product purified by HPLC on a Phenomenex Jupiter C18, 10 μm column using 0–100% gradient elution of water/acetonitrile (containing 0.1% TFA) over 30 minutes at 4 ml/min. The product was obtained as a pink solid (1.9 mg, 50%); λmax (MeOH) 560 nm; m/z (Maldi): 532.

EXAMPLE 7

6,7,9,10-Tetrahydro-2-hydroxyethyl-16,16,18,18-tetramethyl-7aH,8aH-bisindolinium[3,2-a,3'2'-a]pyrano[3,2-c;5,6-c']dipyridin-5-ium (Compound VII)

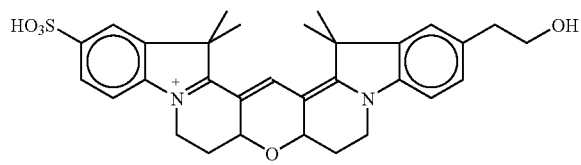

7.1 5-Hydroxyethyl-2,3,3-trimethylindolenine

To a stirred solution of 4-(2-hydroxy)ethyl-aniline (10 g, 73 mmol) in a 3:2 water: conc. HCl (73 ml) solvent mixture at <0° C. was added dropwise a cooled (<0° C.) solution of sodium nitrite (6 g, 73 mmol) in water (86 ml). The reaction mixture was then maintained at the reduced temperature for a further 30 minutes. A saturated solution of sulphur dioxide (150 ml) was added and the reaction warmed to ambient temperature over 1 hour, then warmed for a further hour at 70° C. The reaction mixture was cooled rapidly and the solvent removed in vacuo. The yellow hydrazino intermediate product obtained was redissolved in acetic acid (120 ml) and potassium acetate (16 g, 163 mmol), and methyl-isopropyl ketone (15.5 g, 180 mmol) added at ambient temperature. After 30 minutes the reaction mixture was warmed to 90° C. and stirred for a further 2 hours. The reaction mixture was cooled and the solvent removed in vacuo. The product was dissolved in dichloromethane (100 ml) and washed with water (2×50 ml). The organic phase was dried over MgSO₄, filtered and concentrated in vacuo. The product was purified by HPLC on a Rainin Dynamax C18, 8 μm column using a 0–100% gradient elution of water/acetonitrile (containing 0.1% TFA) over 60 minutes at 20 ml/min. The product was obtained as a yellow oil (1.18 g, 8%); m/z (FAB⁻): 204.1.

7.2 1-(3,3-Diethoxypropyl)-5-hydroxyethyl-2,3,3-trimethylindolenine 1-(3,3-Diethoxypropyl)-5-hydroxyethyl-2,3,3-trimethylindolenine was prepared by reaction of 5-hydroxyethyl-2,3,3-trimethylindolenine (118 mg, 0.072 mmol) with acrolein diethyl acetal (1.13 g, 8.68 mmol), acetic acid (100 μl) in acetonitrile (4 ml) by an analogous method to that described in Section 1.2. The product was purified by HPLC on a Phenomenex Jupiter C18, 10 μm column using a 0–100% gradient elution of water/acetonitrile (containing 0.1% TFA) over 30 minutes at 4 ml/min. The product was obtained as a pale brown oil (24 mg, 12%); m/z (Maldi): 331.

7.3 5-Sulphonato-1-(3,3-diethoxypropyl)-2-(2-N-acetyl-N-phenylamino)ethenyl-2,3,3-trimethylindolenine 5-Sulphonato-1-(3,3-diethoxypropyl)-2-(2-N-acetyl-N-phenylamino)ethenyl-2,3,3-trimethylindolenine was prepared by reaction of 5-sulphonato-1-(3,3'diethoxypropyl)-2,3,3-trimethylindplenine (100 mg, 0.27 mmol) [prepared as described in Section 3.2] with N,N'-diphenylformamidine (79 mg, 0.405 mmol) in acetic anhydride (20 ml) by an analogous method to that described in Section 3.3. The product was not purified, as decomposition was observed. The product was obtained as a yellow oil.

7.4 1-(3,3-Diethoxyoropyl)-5-hydroxyethyl-indocarbocyanine

To a stirred solution of 5-sulphonato-1-(3,3-diethoxypropyl)-2-(2-N-acetyl-N-phenylamino)ethenyl-2,3,3-trimethylindolenine (30 mg, 0.06 mmol) in 4.5:4.5:1 pyridine:acetic acid:acetic anhydride (5 ml) at ambient temperature was added a solution of 1-(3,3'-diethoxypropyl)-5-hydroxyethyl-2,3,3-trimethylindolenine (20 mg, 00.6 mmol) in 4.5:4.5:1 pyridine:acetic acid:acetic anhydride (5 ml). The reaction mixture was warmed to 70° C. for 5 hours. The solution was cooled and the reaction solvent removed in vacuo. The product was purified by HPLC on a Phenomenex Jupiter C18, 10 μm column using a 0–100% gradient elution of water/acetonitrile (containing 0.1% TFA) over 30 minutes at 4 ml/min. The product was obtained as a pink solid (8.6 mg, 10%), λmax (MeOH) 555 nm; m/z (Maldi):712.

7.5 6,7,9,10-Tetrahydro-2-hydroxyethyl-16,16,18, 18-tetramethyl-7aH,8aH-bisindolinium[3,2-a,3'2'-a] pyrano[3,2-c;5,6-c']dipyridin-5-ium 6,7,9,10-Tetrahydro-2-hydroxyethyl-16,16,18,18-tetramethyl-7aH,8aH-bisindolinium[3,2-a,3'2'-a]pyrano[3,2-c;5,6-c']dipyridin-5-ium was prepared by reaction of 1,1-di-(3,3'diethoxypropyl)-5-hydroxyethyl-indocarbocyanine (4.3 mg, 0.06 mmol) in chloroform (5 ml) and 50% sulphuric (1 ml) according to the method described in Section 1.4. The product was purified by HPLC on a Phenomenex Jupiter C18, 10 μm column using a 0–100% gradient elution of water/acetonitrile (containing 0.1% TFA) over 30 minutes at 4 ml/min. The product was obtained as a pink solid (2.8 mg, 90%), λmax 565 nm; m/z (Maldi): 547.

EXAMPLE 8

6,7,8,10-Tetrahydro-14-carboxymethyl-16,16-dimethyl-7a-8a-benzothiozolenine-indolenine-[3,2-a]-benzthiazolyl[3'2'-a]-pyrano[3,2-c;5,6-c']dipyridin-5-ium (Compound VIII)

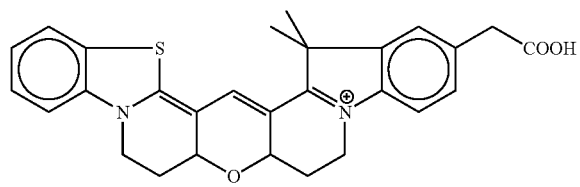

8.1 1-(3,3-Diethoxypropyl)-2-methylbenzothiazole 1-(3,3-Diethoxypropyl)-2-methyl-benzothiazole was prepared by reaction of 2-methylbenzothiazole (125 mg, 0.84 mmol) with acrolein diethyl acetal (1.64 g, 12.6 mmol) and acetic acid (100 μl) in acetonitrile (4 ml) by a method analogous to that described in Section 1.2. The product was purified by HPLC on a Rainin Dynamax C18, 8 μm using a 0–100% gradient elution of water/acetonitrile (containing 0.1% TFA) over 60 minutes at 20 ml/min. The product was obtained as a colourless oil (220 mg, 95%); m/z (FAB⁻): 280.

8.2 5-Carboxymethyl-1-(3,3-diethoxypropyl)-2-(2-N-acetyl-N-phenylamino)ethenyl-2,3,3-trimethylindolenine, ethyl ester 5-Carboxymethyl-1-(3,3-diethoxypropyl)-2-(2-N-acetyl-N-phenylamino)ethenyl-2,3,3-trimethylindolenine, ethyl ester was prepared by reaction of 5-carboxymethyl-1-(3,3-diethoxypropyl)-2,3,3-trimethylindoline, ethyl ester [prepared as described in Section 1.2] (1.16 g, 3.09 mmol) with N,N'-diphenylformamidine (908 mg, 4.63 mmol) in acetic anhydride (25 ml) by a method analogous to that described in Section 3.3. The product was purified by HPLC on a Rainin Dynamax C18, 8 μm column using 10–100% gradient elution of water/acetonitrile (containing 0.1% TFA) over 60 minutes at 20 ml/min. The product was obtained as a pale brown oil (634 mg, 40%). m/z (FAB⁻): 521.

8.3 14-Carboxymethyl-1,1'-di(diethoxyoropyl)-benzthiazolenine-indocarbocyanine, ethyl ester To a stirred solution of 5-carboxymethyl-1-(3,3-diethoxypropyl)-2-(2-N-acetyl-N-phenylamino)ethenyl-2,3,3-trimethylindolenine, ethyl ester (28 mg, 0.054 mmol) in 4.5:4.5:1 pyridine:acetic acid:acetic anhydride (5 ml) at ambient temperature was added a solution of 1-(3,3-diethoxypropyl)-2-methyl-benzothiazole (15.1 mg, 0.054 mmol) in 4.5:4.5:1 pyridine:acetic acid:acetic anhydride (5 ml). The reaction mixture was warmed to 70° C. for 5 hours. The solution was cooled and the reaction solvent removed in vacuo. The product was purified by HPLC on a Phenomenex Jupiter C18, 10 μm column using a 0–100% gradient elution of water/acetonitrile (containing 0.1% TFA) over 30 minutes at 4 ml/min. The product was obtained as a pink solid (14.3 mg, 20%), λmax 549 nm; m/z (FAB⁻): 665.3.

8.4 6,7,8,10-Tetrahydro-14-carboxymethyl-16,16-dimethyl-7a-8a-benzathiozolenine-indolenine-[3,2-a, 3'2'-a]pyrano[3,2-c;5,6-c']dipyridin-5-ium 6,7,8,10-Tetrahydro-14-carboxymethyl-16,16-dimethyl-7a-8a-benzathiozolenine-indolenine-[3,2-a,3'2'-a]pyrano[3,2-c;5,6-c']dipyridin-5-ium was prepared by reaction of (name)(5 mg, 0.0075 mmol) in chloroform (5 ml) and 50% sulphuric acid (1 ml) by an analogous method to that described in section 1.4. The product was purified by HPLC on a Phenomenex Jupiter C18, 10 μm column using a 0–100% gradient elution of water/acetonitrile (containing 0.1% TFA) over 30 minutes at 4 ml/min. The product was obtained as a pink solid (3.2 mg, 90%); λmax 562 nm; m/z (Maldi): 471.

EXAMPLE 9

6,7,8,8a,9,10-Hexahydro-2,14-disulphonato-8-(4-carboxy-anilino)-16,16,18,18-tetramethyl-7aH-bisindolinium[3,2-a;3'2'-a']pyrido[3,2-c;5,6-c']dipyridin-5-ium (Compound IX)

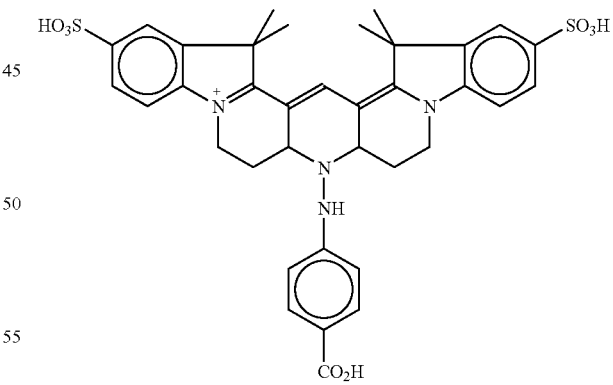

9.1 1,1-Di-(3,3-diethoxypropyl)-5,5'-disulphonato-indocarbocyanine 1,1-Di-(3,3-diethoxypropyl)-5,5'-disulphonato-indolcarbocyanine was prepared by the reaction of 1-diethoxypropyl-5-sulphonato-2,3,3-trimethylindolenine (25.4 mg, 0.069 mmol) [prepared as described in Section 3.2] with triethyl orthoformate (40.7 mg, 0.275 mmol) in pyridine (5 ml) by an analogous method to that described in Section 1.3. The product was purified by HPLC on a Rainin Dynamax C18, 8 µm column using a 0–100% gradient elution of water/acetonitrile over 60 minutes at 20 ml/min. The product was obtained as a pink solid (6.3 mg, 12%); λmax (MeOH) 555 nm; m/z (Maldi): 750.

9.2 6,7,8,8a,9,10-Hexahydro-2,14-disulphonato-8-(4-carboxy-anilino)-16,16,18,18-tetramethyl-7aH-bis-indolinium[3,2-a;3'2'-a']pyrido[3,2-c;5,6-c']dipyridin-5-ium To a stirred solution of 1,1-di-(3,3-diethoxypropyl)-5,5'-disulphonato-indolcarbocyanine (2 mg, 0.0027 mmol) in anhydrous acetic acid (2 ml) was added 4-hydrazinophenyl acetic acid (0.89 mg, 0.0054 mmol) and reaction was warmed to 100° C. After 10 minutes the solution was cooled and the reaction solvent removed in vacuo. The product was purified by HPLC on a Phenomenex Jupiter C18, 10 µm column using a 0–100% gradient elution of water/acetonitrile (containing 0.1% TFA) over 30 minutes at 8 ml/min. The product was obtained as two diastereomeric compounds, both were pink/purple solids (0.04 mg, 2%, 0.06 mg, 3%). λmax (MeOH) 563 nm; m/z (FAB$^+$): 717.21, (FAB$^+$): 717.20.

EXAMPLE 10

6,7,9,10-Tetrahydro-14-carboxymethyl-16,16-dimethyl-7a-8a-quinolino-indolenium-[3,2-a,3'2'-a]-pyrano[3,2-c;5,6-c']dipyridin-5-ium (Compound X)

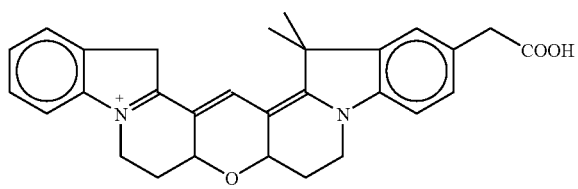

10.1
1-[2-(1,3-Dioxalan-2-yl)ethyl]-2-methyl-quinoline bromide

2-Methyl quinoline (1.6 g, 0.011 mol) and 2-(2-bromoethyl)-1,3-dioxolane (7.7 g, 0.043 mol) were heated together at 85° C. for 16 hrs. On cooling the reaction mixture was diluted with diethyl ether and the resultant solid filtered off, washed with ether and dried. 1-[2-(1,3-dioxalan-2-yl)ethyl]-2-methyl-quinoline bromide was obtained as a brown solid (0.98 g, 27%). m/z (FAB$^-$) 244.

10.2 5-Carboxymethyl-1-(3,3-diethoxypropyl)-2-(2-N-acetyl-N-phenylamino)ethenyl-2,3,3-trimethylindolenine ethyl ester 5-Carboxymethyl-1-(3,3-diethoxypropyl)-2-(2-N-acetyl-N-phenylamino)ethenyl-2,3,3-trimethylindolenine ethyl ester was prepared by reaction of 5-carboxymethyl-1-(3,3-diethoxypropyl)-2,3,3-trimethylindoline ethyl ester [prepared as described in section 1.2] (1.16 g, 3.09 mmol) with N,N'-diphenylformamidine (908 mg, 4.63 mmol) in acetic anhydride (25 ml) by a method analogous to that described in Section 3.3. The product was purified by HPLC on a Rainin Dynamax C18 column using 10–100% gradient elution of water/acetonitrile (containing 0.1% TFA) over 60 minutes at 20 ml/min. The product was obtained as a pale brown oil (634 mg, 40%). m/z (FAB$^+$): 521

10.3 14-Carboxymethyl-1-[2-(1,3-dioxalan-2-yl)ethyl]-1'-(3,3-diethoxypropyl)-quinolino-indocarbocyanine, ethyl ester To a stirred solution of 5-carboxymethyl-1-(3,3-diethoxypropyl)-2-(2-N-acetyl-N-phenylamino)ethenyl-2,3,3-trimethylindolenine ethyl ester (16.1 mg, 0.031 mmol) in ethanol (0.5 ml) at ambient temperature was added a solution of 1-[2-(1,3-dioxalan-2-yl)ethyl]-2-methyl-quinoline-bromide (10 mg, 0.031 mmol) in ethanol (0.5 ml) and triethylamine (125 µl, 0.9 mmol). After 1 hour the reaction solvent was removed in vacuo and the product purified by HPLC on a Phenomenex Jupiter C18, 10 mm column using a 0–100% gradient elution of water/acetonitrile (containing 0.1% TFA) over 30 minutes at 4 ml/min. The product was obtained as a purple solid (10 mg, 51%), λmax 567 nm; m/z (FAB$^-$): 629.

10.4 6,7,9,10-Tetrahydro-14-carboxymethyl-16,16-dimethyl-7a-8a-guinolino-indolenine-[3,2-a,3'2'-a]pyrano[3,2-c;5,6-c']dipyridin-5-ium 6,7,9,10-Tetrahydro-14-carboxymethyl-16,16-dimethyl-7a-8a-quinoline-indolenine-[3,2-a,3'2'-a]pyrano[3,2-c;5,6-c']dipyridin-5-ium was prepared by reaction of (14-carboxymethyl-1-[2-(1,3-dioxalan-2-yl)ethyl]-1'-(3,3-diethoxypropyl)-quinolino-indocarbocyanine, ethyl ester (5 mg, 0.0079 mmol) in chloroform (2 ml) and 50% sulphuric acid (0.4 ml) by an analogous method to that described in section 1.4. The product was purified by HPLC on a Phenomenex Jupiter C18, 10 mm column using a 0–100% gradient elution of water/acetonitrile (containing 0.1% TFA) over 30 minutes at 4 ml/min. The product was obtained as a purple solid (1.6 mg, 44%); λmax 584 nm; m/z (FAB$^+$):465.

EXAMPLE 11

Preparation of Rigid Cy-3-Cy-5 Conjugate (Compound (X))

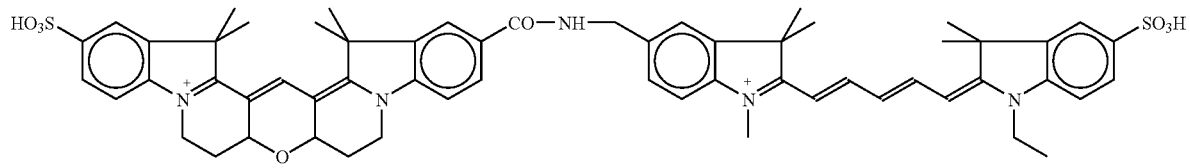

To a mixture of 0-(N-succinimidyl-N,N,N',N'-bis(tetramethylene)uronium hexafluorophosphate (1 mg, 0.0024 mmol), and N,N'-diisopropylethylamine (0.68 mg, 0.007 mmol) in dimethyl sulphoxide (100 µl) at ambient temperature was added 6,7,9,10-tetrahydro-2-carboxymethyl-14-sulphonato-6,16,18,18-tetramethyl-7aH,8aH-bisindolinium[3,2-a,3'2'-a]pyrano[3,2-c;5,6-c']dipyridin-5-ium (1 mg, 0.0018 mmol). After 1 hour diisopropylethylamine (0.23 mg, 0.0018 mmol) and a solution of 5-aminomethyl-5'-sulphonato-1-methyl-1'-ethylindodicarbocyanine (0.9 mg, 0.0018 mmol) in dimethyl sulphoxide (100 µl) was added at ambient temperature. After a further 48 hours the product was purified by HPLC on a Phenomenex Jupiter C18, 10 µm column using a 0–100% gradient elution of water/acetonitrile (containing 0.1% TFA) over 30 minutes at 4 ml/min. The product was obtained as a blue solid; $\lambda_{abs}$ (MeOH) 561 nm and $\lambda_{em}$ 647 nm; m/z (FAB$^-$): 1050.

EXAMPLE 12

Protein:Peptide Polarization Binding Assay

12.1 Synthesis of Labelled Peptide Ligand

A peptide of sequence E-pY-I-N-Q-S-V-P-K (E9K) was prepared by solid phase synthesis on an Applied Biosystems 431 A peptide synthesizer using standard methods and materials. An excess of 6,7,9,10-tetrahydro-2-carboxymethyl-14-sulphonato-16,16,18,18-tetramethyl-7aH,8aH-bisindolinium[3,2-a:3'2'-a']pyrano[3,2-c;5,6-c']dipyridin-5-ium (Compound III), N-hydroxysuccinimide ester was coupled in DMSO in the presence of diisopropylethylamine to the free N-terminus of the protected peptide whilst still attached to the solid phase. After deprotection for two hours, the crude labelled peptide was purified by reverse phase HPLC, using a gradient from water/0.1% TFA to water:acetonitrile (40:60)/0.1% TFA over 60 minutes.

12.2 Binding Assay

Various concentrations of Grb2 glutathione-S-transferase fusion protein and E9K labelled with Compound III in 20 mM MOPS pH7.4/10 mM DTT/005% Tween 20 were incubated in a final volume of 150 µl in black 96-well microplates (Dynatech) for 60 minutes. Non-specific binding was defined using 100 µM unlabelled peptide. Polarization values were read on a Fluorolite FPM2™ plate reader (Jolley Research and Consulting Inc.) using a 530DF30 filter for excitation and 590DF45 filter for emission. The results are shown in FIG. 6 and indicate the specific binding (as determined by change in polarization) of the Compound III-labelled peptide with the Grb2 protein.

EXAMPLE 13

Nucleic Acid FRET Hybridization Assay

13.1 Probe Preparations

Unlabelled target oligonucleotide (5'TAC CCA GAC GAG CAA (SEQ ID NO: 1)-biotin 3') and complementary unlabelled probe oligonucleotide (5' TTG CTC GTC TGG GTA 3' (SEQ ID NO:2)) were synthesised on an Applied Biosystems 391 DNA synthesiser using standard methods and materials. The oligonucleotides were deprotected for 17 hours at 40° C. and purified by reverse phase HPLC using a C18 column and a 40% TEAA/acetonitrile gradient. The desired peaks were collected, freeze dried and the samples were resuspended in sterile H$_2$O.

A second set of target and probe oligonucleotides were synthesised as described, but an amino group was added to the 5' terminal (5'C7 amino-modifier TAC CCA GAC GAG CAA (SEQ ID NO:3)-biotin 3' and 5' C7 amino modifier TTG CTC GTC TGG GTA (SEQ ID NO:4)3').

Amino modified target and probe oligonucleotides were incubated with a 10-fold molar excess of 6,7,9,10-tetrahydro-2-carboxymethyl-14-sulphonato-16,16,18,18-tetramethyl-7aH,8aH-bisindolinium[3,2-a:3'2'-a']pyrano[3,2-c;5,6-c']dipyridin-5-ium (Compound III), N-hydroxysuccinimide ester and Cy5 NHS-ester dye (Amersham Pharmacia Biotech) respectively, in 0.1M sodium bicarbonate buffer (pH9), overnight at 22° C. The following morning, the oligonucleotides were ethanol precipitated and the resulting pellets were resuspended in H$_2$O. Labelled oligonucleotides were purified by reverse phase HPLC using a C18 column and a 60% TEAA/acetonitrile gradient and the desired peaks collected and freeze-dried. Residues were resuspended into H$_2$O and concentration of recovered material was determined.

13.2 Binding Assay

Wells of a black, streptavidin coated 96-well plate were coated with either unlabelled or Compound III-labelled target oligonucleotides (20 pmol/well diluted in 100 µl PBS/1MgCl$_2$) for 120 minutes at ambient temperature. Any unbound material was removed by washing wells vigorously with assay buffer (PBS/1 mM MgCl$_2$/0.1% BSA). Unlabelled or Cy5-labelled probe oligonucleotides were diluted to 0.2 pmol/µl assay buffer, and 100 µl was incubated with coated wells at ambient temperatures for 120 minutes to allow probe hybridisation. Finally, wells were washed vigorously with PBS and fluorescence intensity was measured on a fluorescence plate reader using a 560 nm excitation filter and a 670 nm emission filter (FIG. 7).

Wells coated with unlabelled target oligonucleotide and incubated with either unlabelled or Cy5-labelled probe gave residual background fluorescence signals. Similarly, wells coated with Compound III-labelled target oligonucleotide and incubated with unlabelled probe gave low fluorescence signals. Wells coated with Compound III-labelled target oligonucleotide and incubated with Cy5-labelled probe gave a strong fluorescence signal demonstrating that FRET can occur between Compound III and Cy5.

EXAMPLE 14

Protein:DNA Direct Intensity Binding Assay

14.1 Preparation of Reagents

All HPLC purified oligonucleotides were obtained from Genosys Biotechnologies Ltd. Equimolar amounts of a biotinylated coding strand (5' Biotin-GATCTAGGGACTTTCCGCG (SEQ ID NO:5)3') and an unmodified non-coding strand (5' ATCCCTGAAAGGCGCCTA 3' (SEQ ID NO:6)) specific for NF-kB were incubated together in a boiling water bath for 3 minutes and allowed to anneal by cooling over 2 hours.

Anti-GST antibody (3 mg/ml, 1.5 mg supplied/vial (0.5 ml) from Molecular Probes) was dialysed against 1 litre of 0.15M sodium chloride for 4 hours at room temperature and dialysis was continued overnight at 4° C. in a fresh solution of 0.15M sodium chloride. The following morning the antibody was dialysed against 1 litre of 0.1M sodium hydrogen carbonate for a maximum of 4 hours.

A 1 mg/ml solution of 6,7,9,10-tetrahydro-2-carboxymethyl-14-sulphonato-16,16,18,18-tetramethyl-7aH,8aH-bisindolinium[3,2-a:3'2'-a']pyrano[3,2-c;5,6-c']dipyridin-5-ium (Compound III), N-hydroxysuccinimide ester in DMSO was added gradually with stirring to the antibody at a ratio of 0.10 mg dye:0.33 mg antibody. The solution was mixed for a further 45 minutes at room temperature in the dark. Free dye was removed by dialysis against 1 litre of 0.15M sodium chloride for 4 hours at room temperature and overnight at 40° C. against 1 litre of fresh 0.15M sodium chloride. Finally, the antibody was dialysed against 1 litre of 0.01M PBS/0.01% sodium azide for 4 hours at room temperature and then overnight at 4° C. against 1 litre of 0.01M PBS/0.01% sodium azide. [All dialyses were performed in the dark following labelling.]

14.2 Binding Assay

Biotin-labelled NF-kB-specific dsDNA (2.5 pmol, diluted in 0.01MMgCl$_2$) was added to each well (final volume, 100 µl) of a 96-well streptavidin coated microplate (Boehringer Mannheim) and incubated at room temperature for 2 hours. Following washing with 0.01M phosphate buffer (pH7.5) containing 0.05% Tween 20, 5 pmol/well of p65GST was added in 10 mM Hepes, 0.2 mM sodium acetate, 0.05% NP40, 1 mg/ml BSA and 5 mM DTT (blanks contained no p65GST), in the presence or absence of either 200 pmol/well p65 (specific competitor) or casein (non-specific competitor). Both proteins were diluted in the Hepes buffer as above; final well volume was 100 µl. The plate was agitated at room temperature for 30 minutes and left to stand for a further 30 minutes. Following washing in PBS buffer as above, detection was achieved with 50 pmol/well Compound III-labelled anti-GST Ab in Hepes buffer as above, 100 µl final well volume. Finally, the plate was washed with PBS buffer, as above and 100 µl analar water was added to each well. The plate was read at Ex535/Em569 and Ex560/595 in the Biolumin 960 fluorescence microplate reader (Molecular Dynamics Inc.). The results are shown in FIG. 8.

Detection with Compound III-labelled anti-GST produced a good signal of around 10,000 rfu with a corresponding S/N ratio of between 101:1 (Ex560/Em595) and 123:1 (Ex535/Em569). Specificity was demonstrated using a 40 fold molar excess of a specific competitor, p65 which reduced the total signal by approximately 90%. A non-specific competitor, casein reduced the total signal by only 25%.

EXAMPLE 15

Protein:DNA FRET Binding Assay

15.1 Preparation of Reagents

All HPLC purified NF-kB-specific oligonucleotides were obtained from Genosys Biotechnologies Ltd: a coding strand modified with a 5' terminal primary amine (5' NH$_2$-GATCTAGGGACTTTCCGCG 3' (SEQ ID NO:7)) and an unmodified non-codingstrand (5' ATCCCTGAAAGGCGC-CTAG 3'). A 10-fold molar excess of Cy-5-NHS ester dye (Amersham Pharmacia Biotech) was incubated with the coding strand, in 0.1M sodium bicarbonate buffer (pH9), overnight at 22° C. The following morning the oligonucleotide was ethanol precipitated and then resuspended in water. The labelled coding strand was purified by reverse phase HPLC using a C18 column and a 60% TEAA/acetonitrile gradient. The peak containing labelled oligonucleotide was freeze dried and resuspended in water.

NF-kB-specific double stranded (ds) DNA was generated by incubating together equimolar amounts of the Cy-5 labelled coding strand (5' Cy5-GATCTAGG GACTTTC-CGCG (SEQ ID NO:9)3') and the unmodified non-coding strand (5' ATCCCTGAAA GGCGCCTAG 3' (SEQ ID NO:10)) in a boiling water bath for 3 minutes and allowing to anneal by cooling over 2 hours.

NF-kB p65 protein (260 mg) was diluted to 1000 µl in 0.01M phosphate buffered saline. A 20 fold molar excess of 6,7,9,10-tetrahydro-2-carboxymethyl-14-sulphonato-16,16,18,18-tetramethyl-7aH,8aH-bisindolinium[3,2-a:3'2'-a']pyrano[3,2-c;5,6-c']dipyridin-5-ium (Compound III), N-hydroxysuccinimide ester (as a 1 mg/ml solution in DMSO) was incubated with the protein at 22° C. with agitation for 2 hours (in the dark). The labelled protein was dialysed against three changes of 0.01M phosphate buffered saline/0.5M NaCl/3 mM EDTA/2 mM DTT at 4° C. (in the dark, 4 hours/fresh buffer).

15.2 Binding Assay

A black microtitre plate (Dynatech) was used for the FRET assay. Compound III-labelled p65 (20 pmol) was incubated in 10 mM Hepes, 0.2 mM sodium acetate, 0.05% NP40, 1 mg/ml BSA and 5 mM DTT with 10 pmol of Cy5 labelled NF-kB-specific double stranded (ds) DNA in the presence or absence of either 200 pmol/well p65 (specific competitor) or casein (non-specific competitor). Both proteins were diluted in the Hepes buffer, to give a final well volume of 100 µl. Wells containing Compound III-labelled p65 only were used as the blank. The plate was incubated with agitation for 30 minutes at 22° C. (in the dark) and left to stand for a further 30 minutes. The plate was read at Ex520/Em670 in the Biolumin 960 fluorescence microplate reader (Molecular Dynamics Inc.). The results are shown in FIG. 9.

A signal of 2000 rfu was obtained in the FRET assay with a corresponding S/N ratio of 4:1. Specificity was demonstrated using a 10 fold molar excess of a specific competitor, p65, which reduced the total signal by 40%. A non-specific competitor, casein had no effect on the total signal.

EXAMPLE 16

Receptor Ligand Binding Assay Using Fluorescence Polarization

16.1 Preparation of Reagents

A sample of 6,7,9,10-tetrahydro-2-carboxymethyl-14-sulphonato-16,16,18,18-tetramethyl-7aH,8aH-bisindolinium [3,2-a:3'2'-a']pyrano[3,2-c;5,6-c']dipyridin-5-ium (Compound III), N-hydroxysuccinimide ester (1 mg) was reacted with 1 mg of telenzepine amine congener* in dimethylsulphoxide in the presence of 5% v/v triethylamine. The reaction was allowed to continue for 2 hours at ambient temperature in the dark. The compound III-telenzepine product was purified from the starting material by reverse phase HPLC using a C18 column and a 60% water/acetonitrile gradient in the presence of 0.1% trifluoracetic acid. The product peaks were collected, freeze dried in the dark and resuspended in dimethyl sulphoxide. This was aliquoted and stored frozen at −20° C. in the dark.

*Telenzepine amine congener was provided by Research Biochemicals International as part of the Chemical Synthesis Programme of the National Institute of Mental Health, Contract NO1MH30003.

Chinese hamster ovary cells stably expressing the $M_1$ muscarinic receptor (CHO $M_1$ cells) were grown in HAMS F12 media (Sigma) with 10% foetal bovine serum (BRL); 2 mM glutamine; 50 IU/ml penicillin, streptomycin; 125 µg/ml geneticin (Sigma), maintained at 37° C. with 5% $CO_2$ in a humidified no incubator. The cells were expanded into roller bottles, purged with 5% $CO_2$ and left in a roller bottle incubator at 37° C. for 4 days.

The cells were harvested by scraping into cold phosphate buffered saline pH 7.3 (PBS tablets; Sigma) and pelleted by centrifugation at 1400 rcf at 4° C. in a MSE Mistral 3000 i centrifuge. Cells were resuspended in cold 5 mM $MgCl_2$, 50 mM Tris pH7.5 homogenisation buffer and left on ice for 20 minutes before cell lysis using the Parr cell disruption apparatus (Parr Cat. N°. 4639, 45 ml) using 900 psi of nitrogen. Any non-disrupted cells were removed by centrifugation at 1400 rcf and the supernatant was removed and further centrifuged at 18000 rpm in the Beckman J2-21M/E centrifuge for 20 minutes at 4° C. The resulting pellets were resuspended in cold homogenisation buffer and centrifuged at 18000 rpm as before. The cell membrane pellets were resuspended in approximately 15 ml of homogenisation buffer, aliquoted and frozen in liquid nitrogen for storage at −70° C.

16.2 Binding Assay

Aliquots of CHO $M_1$ cell membrane (50 µg) was added to wells of a black microtitre plate containing a range of dilutions of the $M_1$ muscarinic receptor antagonists atropine and TAC (5000 nM–0.064 nM). The plate was then measured on the Fluorolite FPM-2™ where background polarization values were determined (excitation filter 530 nm; emission filter 590 nm). After addition of Compound III-telenzepine ligand (4 nM final concentration) the plate was sealed and incubated at 22° C. in the dark on a microtitre plate shaker. A final reading was taken after 80 minutes. From the polarization data obtained, competition curves were generated for both atropine and TAC, using non-linear regression and one-site binding analysis (GraphPad Prism 2.0 data manipulation package).

The curves in FIG. 10 show specific polarization readings plotted against $\log_{10}$ molar concentration unlabelled ligand. A specific signal of 190 mP was obtained and the $IC_{50}$ values determined from this experiment were 4.1 nM for atropine and 28 nM for the unlabelled TAC.

The invention claimed is:

1. A compound (I) of formula:

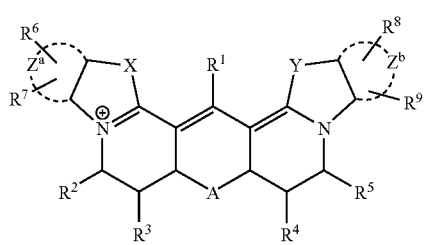

(1)

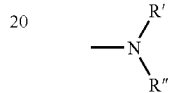

substituted by groups $R^2$–$R^9$, wherein groups $R^6$, $R^7$, $R^8$ and $R^9$ are attached to the atoms of the $Z^a$ and $Z^b$ ring structures;

$R^2$ to $R^9$ are the same or different and are —$R^{10}$ or -L-$R^{10}$ where $R^{10}$ is selected from hydrogen, halogen, amide, $C_1$–$C_6$ alkoxy, nitro, cyano, aryl, heteroaryl, sulphonate, quaternary ammonium, guanidium, hydroxyl, phosphate, phosphonate, optionally substituted amino, azido, sulphydryl, carboxyl, carbonyl and reactive groups selected from succinimidyl ester, isothiocyanate, anhydride, haloacetamide, maleimide, sulphonyl halide, phosphoramidite, acid halide, alkylimidate, hydrazide and carbodiimide, and L is selected from the group consisting of a straight or branched $C_{1-20}$ alkyl chain, a $C_{2-20}$ monoether or polyether and a $C_{2-20}$ atom chain containing up to four secondary amide linkages;

$R^1$ is selected from hydrogen, aryl, heteroaryl, cyano, nitro, aldehyde, halogen, hydroxy, amino, quaternary amino, acetal, ketal, phosphoryl, sulphydryl, and alkyl groups optionally substituted by amino, $C_{1-4}$ alkyl-substituted amino, quaternary amino, aldehyde, ketone, acetal, ketal, halo, cyano, aryl, heteroaryl, hydroxyl, sulphonate, sulphate, carboxylate, amide and nitro;

A is selected from O, S and $NR^{11}$ where $R^{11}$ is the substituted amino radical:

where R' is selected from hydrogen, a $C_{1-4}$ alkyl and aryl and R" is selected from $C_{1-18}$ alkyl, aryl, heteroaryl, an acyl radical having from 2–7 carbon atoms , and a thiocarbamoyl radical;

X and Y may be the same or different and are selected from bis-$C_1$–$C_4$ alkyl and $C_4$–$C_5$ spiro alkyl substituted carbon, oxygen, sulphur, selenium, CH=CH, and N—W wherein N is nitrogen and W is selected from hydrogen, a group —$(CH_2)_nR^{12}$ where n is an integer from 1 to 26 and $R^{12}$ is selected from hydrogen, amino, aldehyde, acetal, ketal, halo, cyano, aryl, heteroaryl, hydroxyl, sulphonate, sulphate, carboxylate, substituted amino, quaternary amino, nitro, primary amide and substituted amide;

$Z^a$ and $Z^b$ each represent the atoms necessary to complete one, or two fused aromatic rings each ring having six carbon atoms;

provided that when X and Y are other than carbon, at least one of $R^2$–$R^9$ represents -L-$R^{10}$ or $R^{10}$ wherein $R^{10}$ is said reactive group or, when X and Y are different and are selected from O and Se, at least one of $R^1$–$R^9$ is other than hydrogen, methyl, phenyl or naphthyl.

2. A compound (I) according to claim 1 wherein $R^1$ is selected from hydrogen, aryl, heteroaryl, cyano, halogen, alkyl groups of twenty-six carbon atoms or less and —$(CH_2)_n$Q where 1<n<26 and Q is selected from amino, aldehyde and hydroxyl and $R^2$, $R^3$, $R^4$ and $R^5$ are hydrogen.

3. A compound selected from:
   i) 6,7,9,10-Tetrahydro-2,14-carboxymethyl-16,16,18,18-tetramethyl-7aH,8aH-bisindolinium[3,2-a;3'2'-a']pyrano[3,2-c;5,6-c']dipyridin-5-ium (Compound I);
   ii) 8,9,11,12-Tetrahydro-3,17-disulphonato-20,20,22,22-tetramethyl-9aH,10aH-bisbenz[e]indolinium[3,2-a,3'2'-a]pyrano[3,2-c;5,6-c']dipyridin-7-ium (Compound II);
   iii) 6,7,9,10-Tetrahydro-2-carboxymethyl-14-sulphonato-16,16,18,18-tetramethyl-7aH,8aH-bisindolinium[3,2-a,3'2'-a]pyrano[3,2-c;5,6-c']dipyridin-5-ium (Compound III);

iv) 6,7,9,10-Tetrahydro-2-carboxymethyl-14-sulphonato-16,16,18,18-tetramethyl-7aH,8aH-bisindolinium[3,2-a,3'2'-a]pyrano[3,2-c;5,6-c']dipyridin-5-ium, glycinamide (Compound IV);

v) 6,7,9,10-Tetrahydro-2-carboxymethyl-14-sulphonato-16,16,18,18-tetramethyl-7aH,8aH-bisindolinium[3,2-a,3'2'-a]pyrano[3,2-c;5,6-c']dipyridin-5-ium, N-(2-aminoethylcarboxamide) (Compound V);

vi) 6,7,9,10-Tetrahydro-2-(N-formyl)aminomethyl-14-sulphonato-16,16,18,18-tetramethyl-7aH,8aH-bisindolinium[3,2-a,3'2'-a]pyrano[3,2-c;5,6-c']dipyridin-5-ium (Compound VI);

vii) 6,7,9,10-Tetrahydro-2-hydroxyethyl-16,16,18,1 8-tetramethyl-7aH,8aH-bisindolinium[3,2-a,3'2'-a]pyrano[3,2-c;5,6-c']dipyridin-5-ium (Compound VII);

viii) 6,7,8,10-Tetrahydro-14-carboxymethyl-16,16-dimethyl-7a-8a-benzothiazolenine-indolenine-[3,2-a]-benzthiazolyl [3'2'-a]-pyrano[3,2-c;5,6-c']dipyridin-5-ium (Compound VIII);

ix) 6,7,8,8a,9,10-Hexahydro-2,14-disulphonato-8-(4-carboxy-anilino)-16,16,18,18-tetramethyl-7aH-bis-indolinium[3,2-a;3'2'-a']pyrido[3,2-c;5,6-c']dipyridin-5-ium (Compound IX);

x) 6,7,9,10-Tetrahydro-14-carboxymethyl-16,16-dimethyl-7a-8a-quinolino-indolenium-[3,2-a,3'2'-a]-pyrano[3,2-c;5,6-c']dipyridin-5-ium (Compound X).

4. A method for producing a compound (I) according to claim 1 or 2 comprising (i) providing a compound (II) of the following formula:

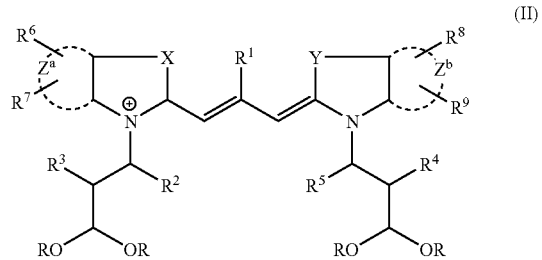

wherein R is methyl or ethyl; and (ii) treating said compound (II) under acid conditions to form the compound of formula (I).

* * * * *